US006855508B2

(12) United States Patent
Fei et al.

(10) Patent No.: US 6,855,508 B2
(45) Date of Patent: Feb. 15, 2005

(54) ELISA FOR VEGF

(75) Inventors: David Tai Wai Fei, Belmont, CA (US); Kristen Tomita, San Mateo, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 10/211,282

(22) Filed: Aug. 5, 2002

(65) Prior Publication Data

US 2003/0044865 A1 Mar. 6, 2003

Related U.S. Application Data

(63) Continuation of application No. 09/713,515, filed on Nov. 15, 2000, now abandoned.
(60) Provisional application No. 60/165,736, filed on Nov. 16, 1999.

(51) Int. Cl.[7] .................. G01N 33/53; G01N 33/545; G01N 33/574; G01N 33/577; C07K 16/22
(52) U.S. Cl. ............. 435/7.92; 435/7.21; 435/7.5; 435/7.94; 435/70.21; 435/452; 435/330; 435/335; 435/337; 435/344; 435/975; 436/518; 436/528; 436/531; 436/548; 436/172; 436/809; 436/813; 530/388.23; 530/388.25; 530/388.8; 530/389.2; 530/389.3; 530/389.7; 530/391.1
(58) Field of Search .................. 435/7.1, 7.21, 435/7.5, 7.92, 7.94, 70.21, 452, 330, 335, 337, 344, 975; 436/518, 528, 531, 548, 172, 809, 813; 530/388.23, 388.25, 388.8, 389.2, 389.3, 389.4, 391.1

(56) References Cited

U.S. PATENT DOCUMENTS

| 3,645,852 A | 2/1972 | Axen et al. |
| 3,691,016 A | 9/1972 | Patel |
| 3,720,760 A | 3/1973 | Bennich et al. |
| 3,969,287 A | 7/1976 | Jaworek et al. |
| 4,195,128 A | 3/1980 | Hildebrand et al. |
| 4,229,537 A | 10/1980 | Hodgins et al. |
| 4,247,642 A | 1/1981 | Hirohara et al. |
| 4,330,440 A | 5/1982 | Ayers et al. |
| 4,376,110 A | 3/1983 | David et al. |
| 5,219,739 A | 6/1993 | Tischer et al. |
| 5,434,087 A | 7/1995 | Beggs et al. |
| 5,620,845 A | 4/1997 | Gould et al. |
| 5,985,579 A | 11/1999 | Buechler et al. |

FOREIGN PATENT DOCUMENTS

| JP | 8245424 | 9/1996 |
| JP | 11178593 | 7/1999 |

OTHER PUBLICATIONS

Aiello et al., "Vascular endothelial growth factor in ocular fluid of patients with diabetic retinopathy and other retinal disorders," *New England J. of Medicine*, vol. 331, No. 22, pp. 1480–1487 (1994).

Anthony et al., "Variation in detection of VEGF in maternal serum by immunoassay and the possible influence of binding proteins," *Ann. Clin. Biochem.*, vol. 34, pp. 276–280 (1997

(List continued on next page.)

*Primary Examiner*—Christopher L. Chin
*Assistant Examiner*—James L. Grun
(74) *Attorney, Agent, or Firm*—Merchant & Gould P.C.

(57) ABSTRACT

The vascular endothelial growth factor (VEGF) activity in a patient's bloodstream or other biological sample can serve as a diagnostic and prognostic index for cancer, diabetes, heart conditions, and other pathologies. Antibody-sandwich ELISA method and kits for VEGF as an antigen were developed to detect VEGF levels in biological samples from animal models and human patients and are used as a diagnostic/prognostic index.

31 Claims, 21 Drawing Sheets

OTHER PUBLICATIONS

Baccala et al., "Serum vascular endothelial growth factor is a candidate biomarker of metastatic tumor response to ex vivo gene therapy of renal cell cancer," *Urology*, vol. 51, No. 2, pp. 327–332 (1998).).

Baker et al., "Elevated serum levels of vascular endothelial growth factor in patients with preeclampsia," *Obstet. Gynecol*, vol. 86, pp. 815–821 (1995).

Banks et al.; "Evidence for the existence of a novel pregnancy–associated soluble variant of the vascular endothelial growth factor receptor, Flt–1," *Molecular Human Reproduction*, vol. 4, No. 4, pp. 377–386 (1998).

Berkman et al.; "Expression of the vascular permeability factor/vascular endothelial growth factor gene in central nervous system neoplasms," *J. Clin. Invest.*, vol. 91, No. 1, pp. 153–159 (1993).

Brekken et al., "Selective Inhibition of Vascular Endothelial Growth Factor (VEGF) Receptor 2 (KDR/Flk–1) Activity by a Monoclonal Anti–VEGF Antibody Blocks Tumor Growth in Mice," *Cancer Research*, vol. 60, pp. 5117–5124 (2000).

Brekken et al., "Vascular Endothelial Growth Factor as a Marker of Tumor Endothelium," *Cancer Research*, vol. 58, pp. 1952–1959 (1998).

Brown et al., "Expression of vascular permeability factor (vascular endothelial growth factor) and its receptors in adenocarcinomas of the gastrointestinal tract," *Cancer Research*, vol. 53, No. 19, pp. 4727–4735 (1993).

Brown et al., "Expression of vascular permeability factor (vascular endothelial growth factor) and its receptors in breast cancer," *Human Pathology*, vol. 26, No. 1, pp. 86–91 (1995).

de Vries et al., "The fms–like tyrosine kinase, a receptor for vascular endothelial growth factor," *Science* vol. 255, pp. 989–991 (1992).

Dvorak et al., "Vascular permeability factor/vascular endothelial growth factor, microvascular hyperpermeability and angiogenesis," *American Journal of Pathology*, vol. 146, No. 5, pp. 1029–1039 (1995).

Ferrara et al., "The biology of vascular endothelial growth factor," *Endocrine Reviews*, vol. 18, No. 1, pp. 4–25 (1997).

Ferrari et al., "Serum and urinary vascular endothelial growth factor levels in non–small cell lung cancer patients," *European Journal of Cancer*, vol. 32A, No. 13, pp. 2368–2369 (1996).

Folkman et al., "Angiogenesis," *Journal of Biological Chemistry*, vol. 267, pp. 10931–10934 (1992).

Fujisaki et al., "Circulating vascular endothelial growth factor in patients with colorectal cancer," *American Journal of Gastroenterology*, vol. 93, No. 2, pp. 249–252 (1998).

Furhmann–Benzakein et al, "Elevated Levels of Angiogenic Cytokines in the Plasma of Cancer Patients," *Int. J. Cancer*, vol. 85, pp. 40–45 (2000).

Gasparini et al., "Prognostic significance of vascular endothelial growth factor protein in node–negative breast carcinoma," *Journal of National Cancer Institute*, vol. 89, No. 2, pp. 139–147 (1997).

Hanatani et al., "Sensitive chemiluminescence enzyme immunoassay for vascular endothelial growth factor/vascular permeability factor in human serum," *Biosci. Biotechnol. Biochem.*, vol. 59, No. 10, pp. 1958–1959 (1995).

Horak et al., "Angiogenesis, assessed by platelet/endothelial cell adhesion molecule antibodies, as indicator of node metastases and survival in breast cancer," *Lancet*, vol. 340, No. 8828, pp. 11204–1124 (1992).

Hornig et al., "Detection and quantification of complexed and free soluble human vascular endothelial growth factor receptor–1 (sVEGFR–1) by ELISA," *J. Immunol. Methods*, vol. 226, pp. 169–177 (1999).

Houck et al., "Dual regulation of vascular endothelial growth factor bioavailability by genetic and proteolytic mechanisms," *Journal of Biological Chemistry*, vol. 267, pp. 26031–26037 (1992).

Houck et al. "The vascular endothelial growth factor family: identification of a fourth molecular species and characterization of alternative splicing of RNA," *Mol. Endocrinol.*, vol. 5, pp. 1806–1814 (1991).

Keck et al., "Disulfide Structure of the Heparin Binding Domain in Vascular Endothelial Growth Factor: Characterization of Posttranslational Modifications in VEGF," *Archives of Biochemistry & Biophysics*, vol. 344, No. 1, pp. 103–113 (1997).

Keyt et al., "Identification of Vascular Endothelial Growth Factor Determinants for Binding KDR and FLT–1 Receptors: Generation of receptor–selective VEGF variants by site–directed mutagenesis," *Journal of Biological Chemistry* vol. 271, No. 10, pp. 5638–5646 (1996).

Keyt et al., "The Carboxyl–terminal Domain (111–165) of Vascular Endothelial Growth Factor Is Critical for Its Mitogenic Potency," *Journal of Biological Chemistry*, vol. 271, No. 13, pp. 7788–7795 (Mar. 29, 1996).

Kim et al., "The Vascular Endothelial Growth Factor Proteins: Identification of Biologically Relevant Regions by Neutralizing Monoclonal Antibodies," *Growth Factors*, vol. 7, No. 1, pp. 53–64 (1992).

Klagsbrun et al., "Regulators of angiogenesis," *Ann. Rev. Physiol.*, vol. 53, pp. 217–239 (1991).

Kohn, E., "Angiogenesis in ovarian carcinoma: a formidable biomarker," *Cancer*, vol. 80, No. 12, pp. 2219–2221 (1997).

Kondo et al., "Vascular endothelial growth factor/vascular permeability factor is detectable in the sera of tumor–bearing mice and cancer patients," *Biochimica et Biophysica Acta*, vol. 1221, No. 2, pp. 211–214 (1994).

Leith et al., "Secretion rates and levels of vascular endothelial growth factor in clone A or HCT–8 human colon tumor cells as a function of oxygen concentration," *Cell Proliferation*, vol. 28, No. 8, pp. 415–430 (1995).

Leung et al., "Vascular Endothelial Growth Factor is a Secreted Angiogenic Mitogen," *Science*, vol. 246, pp. 1306–1309 (1989).

Lin et al., "Preclinical Pharmacokinetics, Interspecies Scaling, and Tissue Distribution of a Humanized Monoclonal Antibody against Vascular Endothelial Growth Factor," *J. Pharm. Exp. Ther.*, vol. 288, No. 1, pp. 371–378 (1999).

Lopez et al., "Transdifferentiated retinal pigment epithelial cells are immunoreactive for vascular endothelial growth factor in surgically excised age–related macular degeneration–related choroidal neovascular membranes," *Invest. Ophthalmol. Vis. Sci.*, vol. 37, No. 5, pp. 855–868 (1996).

Macchiarini et al., "Relation of neovascularisation to metastasis of non–small–cell lung cancer," *Lancet*, vol. 340, No. 8812, pp. 145–146 (1992).

Mattern et al., "Association of vascular endothelial growth factor expression with intratumoral microvessel density and tumour cell proliferation in human epidermoid lung carcinoma," *Brit. J. Cancer*, vol. 73, No. 7, pp. 931–934 (1996).

Menrad et al., "Novel Antibodies Directed Against the Extracellular Domain of the Human VEGF–Receptor Type II," *Hybridoma*, vol. 16, No. 5, pp. 465–471 (1997).

Millauer et al., "High affinity VEGF binding and development expression suggests Flk–1 as a major regulator of vasculogenesis and angiogenesis," *Cell*, vol. 72, pp. 835–846 (1993).

Mordenti et al., "Comparison of the Intraocular Tissue Distribution, Pharmacokinetics and Safety of $^{125}$I–Labeled Full–Length and Fab Antibodies in Rhesus Monkeys Following Intravitreal Administration," *Toxicological Pathology*, vol. 27, No. 5, pp. 536–544 (1999).

Muller et al., "The crystal structure of vascular endothelial growth factor (VEGF) refined to 1.93 A resolution: multiple copy flexibility and receptor binding," *Structure*, vol. 5, No. 10, pp. 1325–1338 (Oct. 1997).

Muller et al., "Vascular endothelial growth factor: crystal structure functional mapping of the kinase domain receptor binding site," *Proc. Natl. Acad. Sci. USA*, vol. 94, No. 14, pp. 7192–7197 (Jul. 8, 1997).

Muller et al., "VEGF and the Fab fragment of a humanized neutralizing antibody: crystal structure of the complex at 2.4 A resolution and mutational analysis of the interface," *Structure*, vol. 6, No. 9, pp. 1153–1167 (Sep. 15, 1998).

Neufeld et al., "Vascular endothelial growth factor (VEGF) and its receptors," *The FASEB Journal*, vol. 13, pp. 9–22 (1999).

Neufeld et al., "Vascular endothelial growth factor and its receptors," *Progress in Growth Factor Research*, vol. 5, No. 1, pp. 89–97 (1994).

Obermair et al., "Concentration of vascular endothelial growth factor (VEGF) in the serum of patients with suspected ovarian cancer," *British Journal of Cancer*, vol. 77, No. 11, pp. 1870–1874 (1998).

Park et al., "The vascular endothelial growth factor (VEGF) isoforms: differential deposition into the subepithelial extracellular matrix and bioactivity of extracellular matrix–bound VEGF," *Mol. Biol. Cell*, vol. 4, pp. 1317–1326 (1993).

Plouet et al., "Isolation and characterization of a newly identified endothelial cell mitogen produced by AtT–20 cells," *EMBO Journal*, vol. 8, No. 12, pp. 3801–3806 (1994).

Rodriguez, C. et al., "A sensitive fluorometric enzyme linked immunosorbent assay that measures vascular endothelial growth factor $_{165}$ in human plasma," *J. Immunol. Methods*, vol. 219, No. 1–2, pp. 45–55 (Oct. 1, 1998).

Rotmans et al., "Cross–linking of Schistosoma mansoni antigens and their covalent binding on the surface of polystyrene microtitration trays for use in the ELISA," *J. Immunol. Methods*, vol. 57, pp. 87–98 (1983).

Shifren et al., "Ovarian steroid regulation of vascular endothelial growth factor in the human endometrium: Implications for angiogenesis during the menstrual cycle and in the pathogenesis of endometriosis," *J. Clin. Endocrinol. Metab.*, vol. 81, No. 8, pp. 3112–3118 (1996).

Takano et al., "Concentration of vascular endothelial growth factor in the serum and tumor tissue of brain tumor patients," *Cancer Research*, vol. 56, No. 9, pp. 2185–2190 (1996).

Terman et al., "Identification of the KDR tyrosine kinase as a receptor for vascular endothelial cell growth factor," *Biochem. & Biophys. Res. Comm.*, vol. 187, pp. 1579–1586 (1992).

Tischer et al., "The human gene for vascular endothelial growth factor. Multiple protein forms are encoded through alternative exon splicing," *Journal of Biological Chemistry*, vol. 266, No. 18, pp. 11947–11954 (1991).

Toi et al., "Quantitative analysis of vascular endothelial growth factor in primary breast cancer," *Cancer*, vol. 77, No. 6, pp. 1101–1106 (1996).

Webb, N. et al., "Vascular endothelial growth factor (VEGF) is released from platelets during blood clotting: Implications for measurement of circulating VEGF levels in clinical disease," *Clinical Science*, vol. 94, No. 4, pp. 395–404 (Apr. 1998).

Weidner et al., "Tumor angiogenesis and metastasis—correlation in invasive breast carcinoma," *New England J. of Medicine*, vol. 324, No. 1, pp. 1–8 (1991).

Wells et al., "Levels of vascular endothelial growth factor are elevated in the vitreous of patients with subretinal neovascularisation," *Brit. J. Opthalmology*, vol. 80, pp. 363–366 (1996).

Yang et al., "Substantially attenuated hemodynamic responses to *Escherichia coli*–derived vascular endothelial growth factor given by intravenous infusion compared with bolus injection," *J. Pharm. Exp. Ther.*, vol. 284, No. 1, pp. 103–110 (1998).

Yeo et al., "Development of time–resolved immunofluorometric assay of vascular permeability factor," *Clinical Chemistry* vol. 38, No. 1, pp. 71–75 (1992).

Yeo et al., "Vascular permeability factor (vascular endothelial growth factor) in guinea pig and human tumor and inflammatory effusions," *Cancer Research*, vol. 53, No. 12, pp. 2912–2918 (1993).

Jelkmann, "Pitfalls in the measurement of circulating vascular endothelial growth factor," *Clin. Chem.* 47: 617–623 (2001).

Schlaeppi et al. "Chemiluminescence immunoassay for vascular endothelial growth factor (vascular permeability factor) in tumor–tissue homogenates," *Clin. Chem.* 42: 1777–1784 (1996).

The Effect of pH to the Multi-Site VEGF ELISA

Dilution Linearity of Normal Human EDTA Plasma spiked with rhVEGF

—— y = 11.043 + 93.774x  R= 0.9965
— - y = 9.7826 + 99.13x  R= 0.99996
— — - y = 9.4783 + 95.513x  R= 0.9987
- - - - y = 11.391 + 77.565x  R= 0.99814
· · · · · y = 10.348 + 84.591x  R= 0.99513
— - - y = 21.522 + 101.29x  R= 0.98729

ELISA FOR VEGF

This application is a continuation of U.S. application Ser. No. 09/713,515, filed Nov. 15, 2000, now abandoned which claims the benefit under 35 U.S.C. §119(e) of U.S. Provisional Application No. 60/165,736, filed Nov. 16, 1999, the entire disclosures of which are hereby expressly incorporated by reference.

BACKGROUND OF THE INVENTION

1. Field of the Invention

This invention relates to immunoassays for detecting VEGF that can be used as diagnostic and prognostic methods for patients with cancer, cardiovascular, or other pathologies.

2. Description of Related Art

It is now well established that angiogenesis is implicated in the pathogenesis of a variety of disorders. These include solid tumors, intra-ocular neovascular syndromes such as proliferative retinopathies or age-related macular degeneration (AMD), rheumatoid arthritis, and psoriasis (Folkman et al *J. Biol. Chem.* 267:10931–10934 (1992); Klagsbrun et al *Annu. Rev. Physiol.* 53:217–239 (1991); and Garner A, *Vascular diseases. In: Pathobiology of ocular disease. A dynamic approach* Garner A, Klintworth G K, Eds. 2nd Edition (Marcel Dekker, N.Y., 1994), pp 1625–1710) In the case of solid tumors, the neovascularization allows the tumor cells to acquire a growth advantage and proliferative autonomy compared to the normal cells. Accordingly, a correlation has been observed between density of microvessels in tumor sections and patient survival in breast cancer as well as in several other tumors (Weidner et al *N Engl J Med* 324:1–6(1991); Horak et al. *Lancet* 340:1120–1124 (1992); and Macchiarini et al. *Lancet* 340:145–146 (1992)).

The search for positive regulators of angiogenesis has yielded many candidates, including aFGF, bFGF, TGF-α, TGF-β, HGF, TNF-α, angiogenin, IL-8, etc. (Folkman et al, supra, and Klagsbrun et al., supra). The negative regulators so far identified include thrombospondin (Good et al *Proc. Natl Acad. Sci. USA.* 87:6624–6628 (1990)), the 16-kilodalton N-terminal fragment of prolactin (Clapp et al. *Endocrinology,* 133:1292–1299 (1993)), angiostatin (O'Reilly et al *Cell* 79:315–328 (1994)), and endostatin (O'Reilly et al. *Cell* 88:277–285 (1996)).

Work done over the last several years has established the key role of vascular endothelial growth factor (VEGF) in the regulation of normal and abnormal angiogenesis (Ferrara et al. *Endocr. Rev.* 18:4–25 (1997)). The finding that the loss of even a single VEGF allele results in embryonic lethality points to an irreplaceable role played by this factor in the development and differentiation of the vascular system (Ferrara et al., supra).

Furthermore, VEGF has been shown to be a key mediator of neovascularization associated with tumors and intra-ocular disorders (Ferrara et al, supra). The VEGF mRNA is overexpressed by the majority of human tumors examined (Berkman et al. *J Clin Invest* 91:153–159 (1993); Brown et al. *Human Pathol.* 26:86–91 (1995); Brown et al. *Cancer Res.* 53:4727–4735 (1993); Mattern et al *Brit. J. Cancer.* 73:931–934 (1996); and Dvorak et al. *Am J. Pathol.* 146:1029–1039 (1995)). Also, the concentration of VEGF in eye fluids is highly correlated to the presence of active proliferation of blood vessels in patients with diabetic and other ischemia-related retinopathies (Aiello et al. *N. Engl. J. Med.* 331:1480–1487 (1994)). Furthermore, studies have demonstrated the localization of VEGF in choroidal neovascular membranes in patients affected by acute macular degeneration (AMD) (Lopez et al. *Invest. Ophtalmo. Vis. Sci.* 37:855–868 (1996)).

VEGF is a heparin binding growth factor with a molecular weight of 45 kD (Plouet et al. *EMBO J.* 8:3801 (1989); Neufeld et al. *Prog. Growth Factor Res.* 5:89 (1994)). It is a dimeric glycoprotein consisting of two identical subunits. Although VEGF is encoded from a single gene, at least five isoforms exist in vivo due to alternative mRNA splicing. These isoforms, VEGF121, VEGF145, VEGF165, VEGF189, and VEGF206, contain 121, 145, 165, 189, and 206 amino acids, respectively (Leung et al. *Science* 246:1306 (1989); Houck et al. *Mol. Endocrinol* 5:1806 (1991); Tischer et al *J. Biol. Chem* 266:11947 (1991); Neufeld et al. *The FASEB Journal* 13:9–22 (1999)). The VEGF isoforms show differing affinities for heparin; VEGF121 binds heparin weakly, while VEGF165, VEGF 189, and VEGF206 bind heparin with increasing affinity. VEGF121 and VEGF165 are secreted and both isoforms are found in the circulation. In contrast, VEGF189 and VEGF206 are found mostly associated with heparin sulfate containing proteoglycans in the extracellular matrix (Houck et al. *J. Biol. Chem.* 267:26031 (1992); Park et al. *Mol. Biol. Cell* 4:1317 (1993)). Of the five isoforms, VEGF165 is the most abundantly expressed variant in the majority of cells and tissues.

Five receptors for VEGF have been identified: VEGFR-1 (FLT-1), VEGFR-2 (KDR/FLK-1), and VEGFR-3, which are all signaling tyrosine kinases, and Neuropilin-1 and Neuropilin-2, which are both accessory-isoform-specific receptors that bind selectively to VEGF165 (de Vries et al. *Science* 255:989 (1992); Terman et al. *Biochem. Biophys Res Commun.* 187:1579(1992); Millauer et al. *Cell* 72:835 (1993); Neufeld et al., supra). The vanous roles of these receptors in VEGF biology are under active investigation by numerous groups.

VEGF is produced by tissues and does not have to enter the circulation to exert its biological effect, but rather acts locally as a paracrine regulator. This raises the question of the significance of circulating VEGF and what role it plays in normal biology or pathology. A recent study by Yang et al. *J. Pharm. Exp. Ther.* 284:103 (1998) found the clearance of rhVEGF165 from the circulation to be very rapid, suggesting endogenous VEGF in the circulation is most likely the result of continual synthesis of VEGF. In addition, several studies have tried to correlate levels of circulating VEGF with tumor burden and have suggested VEGF levels as a potential prognostic marker (Ferran and Scagliotti *Eur. J. Cancer* 32A:2368 (1996); Gasparini et al *J. Natl. Cancer Inst.* 89:139 (1997); Kohn *Cancer* 80:2219 (1997); Baccala et al. *Urology* 51:327 (1998); Fujisaki et al. *Am. J. Gastroenterol.* 93:249 (1998)). Clearly the ability to accurately measure VEGF will be important to understand its potential role(s) in many biological processes, such as maintenance of vascular patency, menstrual cycle, ischemia, diabetes, and cancer.

The literature reports widely varying concentrations of endogenous VEGF in normal and diseased patients, ranging from undetectable to high levels. It has been reported that VEGF 165/165 can be proteolytically cleaved into three other forms: a 165/110 heterodimer, a 110/110 homodimer, and a 55-amino-acid C-terminal fragment (Keyt et al. *J Biol. Chem.* 271:7788–7795 (1996); Keck et al. *Arch. Biochem. Biophys.* 344:103–113 (1997)

The ability to measure endogenous VEGF levels depends on the availability of sensitive and specific assays.

Colorimetric, chemiluminescence, and fluorometric based enzyme-linked immunosorbent assays (ELISAs) for VEGF have been reported. Houck et al., supra, (1992); Yeo et al. *Clin. Chem.* 38:71 (1992); Kondo et al. *Biochim. Biophys. Acta* 1221:211 (1994); Baker el al. *Obstet. Gynecol.* 86:815 (1995);Hanatani el al. *Biosci. Biotechnol. Biochem.* 59:1958 (1995); Leith and Michelson *Cell Prolif.* 28:415 (1995); Shifren et al. *J. Clin Endocrinol. Metab.* 81:3112 (1996); Takano et al. *Cancer Res.* 56:2185 (1996); Toi et al. *Cancer* 77:1101 (1996); Brekken et al. *Cancer Res.* 58:1952 (1998); Obermair et al. *Br. J. Cancer* 77:1870–1874 (1998); Webb et al. *Sci.* 94:395–404 (1998). Similar ELISAs have been successfully applied in the determination of low amounts of drugs and other antigenic components in plasma and urine samples, involve no extraction steps, and are simple to carry out.

The Houck et al., supra (1992) describe a calorimetric ELISA that appears to have ng/ml sensitivity, clearly not sensitive enough to detect endogenous VEGF levels. Yeo et al., supra (1992) describe a two-site time-resolved immunofluorometric assay, however, no VEGF was detected in normal sera (Yeo et al. *Cancer Res.* 53:2912 (1993)). Baker et al, supra (1995), using a modified version of this immunofluorometric assay, reported detectable levels of VEGF in plasma from pregnant women, with higher levels observed in women with preeclampsia. Similar data in pregnant women were reported by Anthony et al. *Ann. Clin. Biochem* 34:276 (1997) using a radioimmunoassay. Hanatani et al., supra (1995) developed a chemiluminescent ELISA capable of measuring circulating VEGF and report VEGF levels in sera from 30 normal individuals (male and female) from 8–36 pg/ml. Brekken et al, supra (1998) described ELISA assays using antibodies having binding preference to either the VEGF alone or the VEGF:Flk-1 complex.

An ELISA kit for VEGF detection is commercially available from R&D Systems (Abingdon, U.K.). The R&D VEGF ELISA kit has been used in sandwich assays wherein a monoclonal antibody is used to capture the target VEGF antigen and a polyclonal antibody is used to detect the VEGF. Webb et al. supra (1998). It is not clear whether the detection results using the R&D ELISA kit are influenced by the presence of proteolytical processes or degradation of VEGF, or by interference of other serum proteins. Obermair et al, supra (1998).

Keyt et al. *J. Biol. Chem.* 271:7788–7795 (1996); Keyt et al. *J. Biol. Chem.* 271:5638 (1996); and Shifren et al, supra (1996) also developed a colorimetric ELISA based on a dual monoclonal antibody pair. Although this ELISA was able to detect elevated VEGF levels in cancer patients, it lacked the sensitivity needed to measure endogenous levels of VEGF in normal individuals. Rodriguez et al. *J. Immunol. Methods* 219:45 (1998) described a two-site fluorimetric VEGF ELISA that yields a sensitivity of 10 pg/ml VEGF in neat plasma or serum. However, this fluorimetric assay can only detect fully intact 165/165 and 165/110 species of VEGF.

Thus, there is a need to develop a diagnostic and prognostic assay that detects higher measurable levels of VEGF in a biological sample of an animal model or patient than existing ELISAs, and can measure all the isoforms of VEGF.

SUMMARY OF THE INVENTION

A multi-site antibody-sandwich ELISA method and kits for VEGF as antigen were developed to detect VEGF in biological samples and used as a diagnostic/prognostic index. Compared to the currently used VEGF ELISAs, the present assay has high sensitivity and is capable of detecting most of the isoforms of endogenous VEGF in circulation.

Specifically, the invention provides a method for detecting VEGF in a biological sample, preferably from vascular, diabetic, or cancer patients, comprising the steps of:

(a) contacting and incubating the biological sample with pre-mixed capture reagents immobilized to a solid support, wherein the capture reagents are polyclonal and monoclonal antibodies against human VEGF, said monoclonal antibody binding specifically to the C-terminal (residues 111–165) of human VEGF;

(b) separating the biological sample from the immobilized capture reagents;

(c) contacting the immobilized capture reagents with a detectable antibody that binds to the KDR and FLT1 receptor binding domains of VEGF; and (d) measuring the level of VEGF bound to the capture reagents using a detection means for the detectable antibody.

Preferably, the capture reagents are immobilized in a weight ratio of about 0.8:1 to 1.2:1 of monoclonal to polyclonal antibody. More preferably, the weight ratio is about 1:1 of monoclonal to polyclonal antibody.

In another aspect, the invention provides an immunoassay kit for detecting VEGF in a biological sample, the kit comprising:

(a) as capture reagents, polyclonal and monoclonal antibodies against human VEGF premixed in a weight ratio of about 0.8:1 to 1.2:1 of monoclonal to polyclonal antibody, wherein the monoclonal antibody binds specifically to the C-terminal (residues 111–165) of human VEGF; and (b) as detection reagent, a detectable antibody that binds to the KDR and FLT1 receptor binding domains of VEGF.

The assay herein is unique in that it uses a polyclonal/monoclonal antibody mixture as the capture reagents, and the capture monoclonal antibody binds to the C-terminal portion of VEGF. Most of the previously disclosed VEGF ELISAs are based on either a dual monoclonal antibody pair for capture/detection, or a monoclonal antibody as capture reagent and a polyclonal antibody for detection. If a polyclonal antibody is used alone as the capture antibody, all sensitivity of the assay is lost. The ability of the monoclonal capture antibody to bind the VEGF C-terminus ensures that all the endogenous VEGF molecules, including 165/165, 165/110 and 110/110 can be detected by the assay described herein. Furthermore, the detection antibody of the invention binds to the biologically active regions of VEGF, i.e., the binding domains for the KDR and FLT1 receptors of VEGF, which ensures that the detected VEGF molecules are free from being blocked by, for example, soluble VEGF receptors in the circulation. As such, the assay described herein provides a more accurate measurement of circulating VEGF molecules that are most likely biologically active.

DESCRIPTION OF THE DRAWINGS

FIGS. 8A–8C show linearity of normal rat EDTA plasma samples spiked with rhVEGF, wherein FIG. 8A shows high spike, FIG. 8B shows mid-spike, and FIG. 8C shows low spike, and wherein the circles are rat pool 1, the squares are rat pool 2, and the diamonds are rat 1.

FIG. 10A shows the specificity of the single-site ELISA using MAb 3.5F8 as coat and detection antibody (FIG. 10A), FIG. 10B shows the specificity of the two-site fluorimetric VEGF ELISA assay using MAb 3.5F8 as coat and MAb A4.6.1 as detection antibody, and FIG. 10C shows the specificity of the multi-site VEGF ELISA herein using MAb 3.5F8 and PAb as coat antibodies and MAb A4.6.1 as detection antibody.

FIG. 16A shows correlation of plasma VEGF measured by the two-site ELISA using MAb 3.5F8 as the coat reagent (x-axis) with plasma VEGF measured by a multi-site assay with MAb 3.5F8 and a polyclonal antibody to DNase as the coat reagents (filled circles), and with plasma VEGF measured by a multi-site assay as set forth herein using MAb 3.5F8 and the PAb to VEGF as the coat reagents (open circles). FIG. 16B shows the standard curves of the two-site ELISA (filled circles), the multi-site ELISA with MAb 3.5F8 and a polyclonal antibody to DNase as the coat reagents (filled diamonds), and a multi-site assay as set forth herein using MAb 3.5F8 and the PAb to VEGF as the coat reagents (filled squares).

DETAILED DESCRIPTION OF THE PREFERRED EMBODIMENTS

A. Definitions

Figure 1:
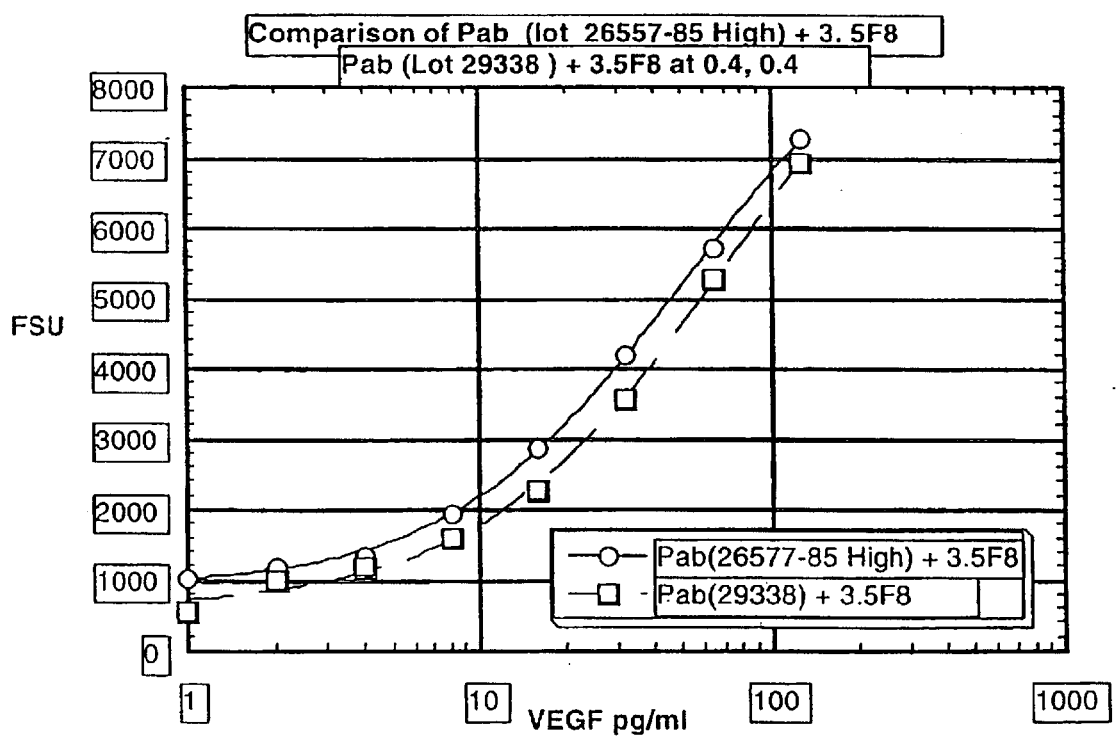
FIG. 1 shows a comparison of two different preparations of affinity-purified rabbit polyclonal antibody against rhVEGF, with the squares depicting the preferred antibody and the circles representing the same antibody from a different bleed.

The term "VEGF" as used herein refers to the 165-amino acid vascular endothelial cell growth factor, and related 121-, 145-, 189-, and 206-amino acid vascular endothelial cell growth factors, as described by Leung et al *Science* 246:1306 (1989), Houck et al. *Mol. Endocrin.* 5:1806 (1991), and Neufeld et al., supra, together with the naturally occurring allelic and processed forms of those growth factors.

The term "detecting" is used in the broadest sense to include both qualitative and quantitative measurements of a target molecule. In one aspect, the detecting method as described herein is used to identify the mere presence of VEGF in a biological sample. In another aspect, the method is used to test whether VEGF in a sample is at a detectable level. In yet another aspect, the method can be used to quantify the amount of VEGF in a sample and further to compare the VEGF levels from different samples The term "biological sample" refers to a body sample from any animal, but preferably is from a mammal, more preferably from a human. Most preferably, such biological sample is from vascular, diabetic, or cancer patients. Such samples include biological fluids such as serum, plasma, vitreous fluid, lymph fluid, synovial fluid, follicular fluid, seminal fluid, amniotic fluid, milk, whole blood, urine, cerebro-spinal fluid, saliva, sputum, tears, perspiration, mucus, and tissue culture medium, as well as tissue extracts such as homogenized tissue, and cellular extracts. The preferred biological sample herein is serum, plasma or urine.

The term "capture reagent" refers to a reagent capable of binding and capturing a target molecule in a sample such that under suitable condition, the capture reagent-target molecule complex can be separated from the rest of the sample. Typically, the capture reagent is immobilized or immobilizable. In a sandwich immunoassay, the capture reagent is preferably an antibody or a mixture of different antibodies against a target antigen.

The term "detectable antibody" refers to an antibody that is capable of being detected either directly through a label amplified by a detection means, or indirectly through, e.g., another antibody that is labeled. For direct labeling, the antibody is typically conjugated to a moiety that is detectable by some means. The preferred detectable antibody is biotinylated antibody.

The term "detection means" refers to a moiety or technique used to detect the presence of the detectable antibody in the ELISA herein and includes detection agents that amplify the immobilized label such as label captured onto a microtiter plate. Preferably, the detection means is a fluorimetric detection agent such as avidin or streptavidin.

The term "antibody" is used in the broadest sense and includes monoclonal antibodies (including agonist, antagonist, and neutralizing antibodies), polyclonal antibodies, multivalent antibodies, multispecific antibodies, and antibody fragments so long as they exhibit the desired binding specificity.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. *Nature* 256:495 (1975), or may be made by recombinant DNA methods (see, e g., U.S. Pat. No. 4,816,567). The "monoclonal antibodies" may also be isolated from phage antibody libraries using the techniques described in Clackson et al *Nature* 352:624–628 (1991) and Marks et al. *J. Mol. Biol.* 222:581–597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al. *Proc. Natl. Acad. Sci USA* 81:6851–6855 (1984)).

"Humanized" forms of non-human (e.g., murine) antibodies are chimeric antibodies that contain minimal sequence derived from non-human immunoglobulin For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al. *Nature* 321:522–525 (1986); Reichmann et al. *Nature* 332:323–329 (1988); and Presta *Curr. Op. Struct. Biol.* 2:593–596 (1992).

"Mammal" for purposes of treatment refers to any animal classified as a mammal, including humans, domestic, and farm animals, and zoo, sports, or pet animals, such as dogs, horses, cats, sheep, pigs, cows, etc. Preferably, the mammal is human.

The terms "cancer", "cancerous", and "malignant" refer to or describe the physiological condition in mammals that is typically characterized by unregulated cell growth. Examples of cancer include but are not limited to, carcinoma including adenocarcinoma, lymphoma, blastoma, melanoma, sarcoma, and leukemia. More particular examples of such cancers include squamous cell cancer, small-cell lung cancer, non-small cell lung cancer, gastrointestinal cancer, Hodgkin's and non-Hodgkin's lymphoma, pancreatic cancer, glioblastoma, cervical cancer, ovarian cancer, liver cancer such as hepatic carcinoma and hepatoma, bladder cancer, breast cancer, colon cancer, colorectal cancer, endometrial carcinoma, salivary gland carcinoma, kidney cancer such as renal cell carcinoma and Wilms' tumors, basal cell carcinoma, melanoma, prostate cancer, vulval cancer, thyroid cancer, testicular cancer, esophageal cancer, and various types of head and neck cancer. The preferred cancers for treatment herein are breast, colon, lung, and melanoma.

The phrases "vascular" and "cardiovascular" are used interchangeably and describe patients with indications that stimulate angiogenesis and/or cardiovascularization, and those that inhibit angiogenesis and/or cardiovascularization Such disorders include, for example, arterial disease, such as atherosclerosis, hypertension, inflammatory vasculitis, Reynaud's disease and Reynaud's phenomenon, aneurysms, and arterial restenosis; venous and lymphatic disorders such as thrombophlebitis, lymphangitis, and lymphedema; and other vascular disorders such as peripheral vascular disease, cancer such as vascular tumors, e g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma, tumor angiogenesis, trauma such as wounds, burns, and other injured tissue, implant fixation, scarring, ischemia reperfusion injury, rheumatoid arthritis, cerebrovascular disease, renal diseases such as acute renal failure, and osteoporosis. This would also include angina, myocardial infarctions such as acute myocardial infarctions, cardiac hypertrophy, and heart failure such as congestive heart failure (CHF).

The term "diabetes" refers to a progressive disease of carbohydrate metabolism involving inadequate production or utilization of insulin and is characterized by hyperglycemia and glycosuria. This term includes all forms of diabetes, such as type I and type II diabetes and insulin-resistant diabetes, such as Mendenhall's Syndrome, Werner Syndrome, leprechaunism, lipoatrophic diabetes, and other lipoatrophies.

The term "affinity purified" refers to purifying a substance by eluting it through an affinity chromatography column.

B. Modes for Carrying Out the Invention

The assay described herein is a multi-site immunoassay utilizing the following steps.

First Step

In the first step of the assay herein, the biological sample is contacted and incubated with the immobilized capture (or coat) reagents, which are an and-VEGF monoclonal antibody and a polyclonal antibody directed against VEGF. These antibodies may be from any species, but preferably the monoclonal antibody is a murine or rat monoclonal antibody, more preferably murine, and most preferably MAb 3.5F8 (Rodriguez et al, supra (1998)), and the polyclonal antibody is rabbit anti-VEGF or goat anti-VEGF antibody, more preferably rabbit anti-VEGF. Furthermore, the polyclonal antibody is preferably affinity purfied, to decrease background. Hence, in a specific preferred embodiment, the immobilized monoclonal antibody is a murine monoclonal antibody, most preferably MAb 3.5F8, and the immobilized polyclonal antibody is an affinity-purified rabbit antibody. The immobilized capture reagents are mixed together before they are immobilized. Immobilization conventionally is accomplished by insolubilizing the capture reagents either before the assay procedure, as by adsorption to a water-insoluble matrix or surface (U.S. Pat. No. 3,720,760) or non-covalent or covalent coupling (for example, using glutaraldehyde or carbodiimide cross-linking, with or without prior activation of the support with, e.g., nitric acid and a reducing agent as described in U.S. Pat. No. 3,645,852 or in Rotmans et al *J Immunol. Methods* 57:87–98 (1983)), or afterward, e.g., by immunoprecipitation.

The solid phase used for immobilization may be any inert support or carrier that is essentially water insoluble and useful in immunometric assays, including supports in the form of, e.g., surfaces, particles, porous matrices, etc. Examples of commonly used supports include small sheets, Sephadex, polyvinyl chloride, plastic beads, and assay plates or test tubes manufactured from polyethylene, polypropylene, polystyrene, and the like including 96-well microtiter plates, as well as particulate materials such as filter paper, agarose, cross-linked dextran, and other polysaccharides. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are suitably employed for capture reagent immobilization In a preferred embodiment the immobilized capture reagents are coated on a microtiter plate, and in particular the preferred solid phase used is a multi-well microtiter plate that can be used to analyze several samples at one time. The most preferred is a microtest 96-well ELISA plate such as that sold as Nune Maxisorb or Immulon.

The solid phase is coated with the pre-mixed capture reagents as defined above, which may be linked by a non-covalent or covalent interaction or physical linkage as desired Techniques for attachment include those described in U.S. Pat. No. 4,376,110 and the references cited therein. If covalent, the plate or other solid phase is incubated with a cross-linking agent together with the capture reagent under conditions well known in the art such as for 1 hour at room temperature.

Commonly used cross-linking agents for attaching the pre-mixed capture reagents to the solid phase substrate include, e.g, 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates capable of forming cross-links in the presence of light.

If 96-well plates are utilized, they are preferably coated with the mixture of capture reagents (typically diluted in a buffer such as 0.05 M sodium carbonate by incubation for at least about 10 hours, more preferably at least overnight, at temperatures of about 4–20° C., more preferably about 4–8° C., and at a pH of about 8–12, more preferably about 9–10, and most preferably about 9.6. If shorter coating times (1–2 hours) are desired, one can use 96-well plates with nitrocellulose filter bottoms (Millipore MULTISCREEN™) or coat at 37° C. The plates may be stacked and coated long in advance of the assay itself, and then the assay can be carried out simultaneously on several samples in a manual, semi-automatic, or automatic fashion, such as by using robotics.

The coated plates are then typically treated with a blocking agent that binds non-specifically to and saturates the binding sites to prevent unwanted binding of the free ligand to the excess sites on the wells of the plate. Examples of appropriate blocking agents for this purpose include, e.g., gelatin, bovine serum albumin, egg albumin, casein, and non-fat milk. The blocking treatment typically takes place under conditions of ambient temperatures for about 1–4 hours, preferably about 1.5 to 3 hours.

After coating and blocking, the VEGF standard (purified VEGF) or the biological sample to be analyzed, appropriately diluted, is added to the immobilized phase. The preferred dilution rate is about 5–15%, preferably about 10%, by volume. Buffers that may be used for dilution for this purpose include (a) PBS containing 0.5% BSA, 0.05% TWEEN 20™ detergent (P20), 0.05% PROCLIN™ 300 antibiotic, 5 mM EDTA, 0.25% Chaps surfactant, 0.2% beta-gamma globulin, and 0.35M NaCl; (b) PBS containing 0.5% BSA, 0.05% P20, and 0.05% PROCLIN™ 300, pH 7; (c) PBS containing 0.5% BSA, 0.05% P20, 0.05% PROCLIN™ 300, 5 mM EDTA, and 0.35 M NaCl, pH 6.35; (d) PBS containing 0.5% BSA, 0.05% P20, 0.05% PROCLIN™ 300, 5 mM EDTA, 0.2% beta-gamma globulin, and 0.35 M NaCl; and (e) PBS containing 0.5% BSA, 0.05% P20, 0.05% PROCLIN™ 300, 5 mM EDTA, 0.25% Chaps, and 0.35 M NaCl Buffer (c) is the preferred buffer for the assay herein since it has the best differentiation between each standard as well as the biggest signal-to-noise ratio. PROCLIN™ 300 acts as a preservative, and TWEEN 20™ acts as a detergent to eliminate non-specific binding. The added EDTA and salt of buffer (c) act to decrease the background over the other buffers, including buffer (b).

The weight ratio of the capture reagents (monoclonal antibody to polyclonal antibody) is preferably about 0.8:1 to about 1.2:1, more preferably about 1:1. The amount of capture reagents employed is sufficiently large to give a good signal in comparison with the VEGF standards, but not in molar excess compared to the maximum expected endogenous VEGF level in the sample. For sufficient sensitivity, it is preferred that the amount of biological sample added be such that the immobilized capture reagents are in molar excess of the maximum molar concentration of free VEGF anticipated in the biological sample after appropriate dilution of the sample. This anticipated level depends mainly on any known correlation between the concentration levels of the free VEGF in the particular biological sample being analyzed with the clinical condition of the patient. Thus, for example, cancer patients may have a maximum expected concentration of free VEGF in their serum that is quite high, whereas a normal child or adult will be expected to have a much lower level of free VEGF in their serum based on what is known in the literature.

If too much of the capture reagents are present, however, the capture reagents will compete with the anti-VEGF present in the biological sample for the bound VEGF, yielding inaccurate results. Thus, while the concentration of the capture reagents will generally be determined by the concentration range of interest of the VEGF taking any necessary dilution of the biological sample into account, the final concentration of the capture reagents will normally be determined empirically to maximize the sensitivity of the assay over the range of interest. However, as a general guideline, the molar excess is suitably less than about ten-fold of the maximum expected molar concentration of free VEGF in the biological sample after any appropriate dilution of the sample. Most preferably, the amount of monoclonal antibodies immobilized is about 0.4 µg/ml and the amount of polyclonal antibodies immobilized is about 0.4 µg/ml.

The conditions for incubation of sample and immobilized capture reagent are selected to maximize sensitivity of the assay and to minimize dissociation. Preferably, the incubation is accomplished at fairly constant temperatures, ranging from about 0° C. to about 40° C., preferably from about 36 to 38° C. to obtain a less variable, lower coefficient of variant (CV) than at, e.g, room temperature. The time for incubation depends primarily on the temperature, being generally no greater than about 10 hours to avoid an insensitive assay. Preferably, the incubation time is from about 0.5 to 3 hours, and more preferably 1.5–3 hours at 36–38° C. to maximize binding of to capture reagents. The duration of incubation may be longer if a protease inhibitor is added to prevent proteases in the biological fluid from degrading the VEGF.

At this stage, the pH of the incubation mixture will ordinarily be in the range of about 6–9.5, preferably in the range of about 6–7, more preferably about 6.0 to 6.5, and most preferably the pH of the assay (ELISA) diluent is 6.35±0.1. Acidic pH such as pH 4–5 decreased recovery of VEGF. The pH of the incubation buffer is chosen to maintain a significant level of specific binding of the capture reagents to the VEGF being captured. Various buffers may be employed to achieve and maintain the desired pH during this step, including borate, phosphate, carbonate, Tris-HCl or Tns-phosphate, acetate, barbital, and the like. The particular buffer employed is not critical to the invention, but in individual assays one buffer may be preferred over another.

Second Step

In the second step of the assay method herein, the biological sample is separated (preferably by washing) from the immobilized capture reagents to remove uncaptured VEGF. The solution used for washing is generally a buffer ("washing buffer") with a pH determined using the considerations and buffers described above for the incubation step, with a preferable pH range of about 6–9. The washing may be done three or more times. The temperature of washing is generally from refrigerator to moderate temperatures, with a constant temperature maintained during the assay period, typically from about 0–40° C., more preferably about 4–30° C. For example the wash buffer can be placed in ice at 4° C. in a reservoir before the washing, and a plate washer can be utilized for this step A cross-linking agent or other suitable agent may also be added at this stage to allow the now-bound VEGF to be covalently attached to the capture reagents if there is any concern that the captured VEGF may dissociate to some extent in the subsequent steps.

Third Step

In the next step, the immobilized capture reagents are contacted with detectable antibodies, preferably at a temperature of about 20–40° C., more preferably about 36–38° C., with the exact temperature and time for contacting the two being dependent primarily on the detection means employed. For example, when 4-methylumbelliferyl-β-galactoside (MUG) and streptavidin-β-galactosidase are used as the means for detection, preferably the contacting is carried out overnight (e.g., about 15–17 hours or more) to amplify the signal to the maximum. While the detectable antibody may be a polyclonal or monoclonal antibody, preferably it is a monoclonal antibody, more preferably murine, and most preferably MAb A4.6.1. Also, the preferred detectable antibody is directly detectable, and preferably has a fluorimetric label. The fluorimetric label has greater sensitivity to the assay compared to the conventional colorimetric label. More preferably, the detectable antibody is biotinylated and the detection means is avidin or streptavidin-β-galactosidase and MUG.

Preferably a molar excess of an antibody with respect to the maximum concentration of free VEGF expected (as described above) is added to the plate after it is washed This antibody (which is directly or indirectly detectable) is preferably a polyclonal antibody, although any antibody can be employed. The affinity of the antibody must be sufficiently high that small amounts of the free VEGF can be detected, but not so high that it causes the VEGF to be pulled from the capture reagents.

Fourth Step

In the last step of the assay method, the level of free VEGF that is now bound to the capture reagents is measured using a detection means for the detectable antibody. If the biological sample is from a vascular, diabetic, or cancer patient, the measuring step preferably comprises comparing the reaction that occurs as a result of the above three steps with a standard curve to determine the level of VEGF compared to a normal individual.

Antibody Production

Polyclonal antibodies to the VEGF generally are raised in animals by multiple subcutaneous (sc) or intraperitoneal (ip) injections of the VEGF and an adjuvant. It may be useful to conjugate the VEGF or a fragment containing the target amino acid sequence to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N$=C=NR, where R and $R^1$ are different alkyl groups.

The antibodies used as the coat or detectable antibodies may be obtained from any convenient vertebrate source, such as murine, primate, lagomorpha, goat, rabbit, rat, chicken, bovine, ovine, equine, canine, feline, or porcine. Chimeric or humanized antibodies may also be employed, as described, e.g., in U.S. Pat. No. 4,816,567; Morrison et al. *Proc. Natl Acad. Sci. USA* 81:6851 (1984); Neuberger et al. *Nature* 312: 604 (1984); Takeda et al. *Nature* 314:452 (1985); and WO 98/45331 published Oct. 15, 1998, as well as in those additional references set forth above.

Animals may be immunized against the immunogenic conjugates or derivatives by combining 1 mg or 1 µg of conjugate (for rabbits or mice, respectively) with 3 volumes of Freund's complete adjuvant and injecting the solution intradermally at multiple sites. One month later the animals are boosted with ⅕ to ⅒ the original amount of conjugate in Freund's incomplete adjuvant by subcutaneous injection at multiple sites. 7 to 14 days later animals are bled and the serum is assayed for anti-VEGF titer. Animals are boosted until the titer plateaus. Preferably, the animal is boosted with the conjugate of VEGF, but conjugated to a different protein and/or through a different cross-linking agent. Conjugates also can be made in recombinant cell culture as protein fusions. Also, aggregating agents such as alum are used to enhance the immune response. Methods for the production of polyclonal antibodies are described in numerous immunology textbooks, such as Davis et al. *Microbiology,* 3rd Edition, (Harper & Row, New York, N.Y., 1980).

Monoclonal antibodies are prepared by recovering spleen cells from immunized animals and immortalizing the cells in conventional fashion, e.g by fusion with myeloma cells or by Epstein-Barr virus transformation, and screening for clones expressing the desired antibody. See, e.g., Kohler and Milstein *Eur. J. Immunol.* 6:511 (1976). Monoclonal antibodies, or the antigen-binding region of a monoclonal antibody, such as Fab or (Fab)$_2$ fragments, may alternatively be produced by recombinant methods.

Examples of suitable antibodies include those already utilized in known RIAs for the protein in question, e.g., those antibodies directed against VEGF as described in the references given in the introduction herein.

Detection

The antibody added to the immobilized capture reagents will be either directly labeled, or detected indirectly by addition, after washing off of excess first antibody, of a molar excess of a second, labeled antibody directed against IgG of the animal species of the first antibody. In the latter, indirect assay, labeled antisera against the first antibody are added to the sample so as to produce the labeled antibody in situ.

The label used for either the first or second antibody is any detectable functionality that does not interfere with the binding of free VEGF to the antibody. Examples of suitable labels are those numerous labels known for use in immunoassay, including moieties that may be detected directly, such as fluorochrome, chemiluminscent, and radioactive labels, as well as moieties, such as enzymes, that must be reacted or derivatized to be detected. Examples of such labels include the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e g., firefly luciferase and bacterial luciferase (U.S. Pat. No. 4,737,456), luciferin, 2,3-dihydrophthalazinediones, horseradish peroxidase (HRP), alkaline phosphiatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HPP, lactoperoxidase, or microperoxidase, biotin/avidin, biotin/streptavidin, biotin/Streptavidin-β-galactosidase with MUG, spin labels, bacteriophage labels, stable free radicals, and the like. As noted above, the fluorimetric detection is preferred.

Conventional methods are available to bind these labels covalently to proteins or polypeptides. For instance, coupling agents such as dialdehydes, carbodiimides, dimaleimides, bis-imidates, bis-diazotized benzidine, and the like may be used to tag the antibodies with the above-described fluorescent, chemiluminescent, and enzyme labels See, for example, U.S. Pat. Nos. 3,940,475 (fluorimetry) and 3,645,090 (enzymes); Hunter et al *Nature* 144:945 (1962); David et al. *Biochemistry* 13:1014–1021 (1974); Pain et al. *J. Immunol Methods* 40:219–230 (1981); and Nygren *J. Histochem and Cytochem* 30:407–412 (1982). Preferred labels herein are fluorescent to increase amplification and sensitivity to 8 pg/ml, more preferably biotin with streptavidin-β-galactosidase and MUG for amplifying the signal.

The conjugation of such label, including the enzymes, to the antibody is a standard manipulative procedure for one of ordinary skill in immunoassay techniques. See, for example, O'Sullivan et al. "Methods for the Preparation of Enzyme-antibody Conjugates for Use in Enzyme Immunoassay," in *Methods in Enzymology*, ed. J. J. Langone and H. Van Vunakis, Vol. 73 (Academic Press, New York, N.Y., 1981), pp. 147–166.

Following the addition of last labeled antibody, the amount of bound antibody is determined by removing excess unbound labeled antibody through washing and then measuring the amount of the attached label using a detection method appropriate to the label, and correlating the measured amount with the amount of free VEGF in the biological sample. For example, in the case of enzymes, the amount of color developed and measured will be a direct measurement of the amount of VEGF present. Specifically, if HRP is the label, the color is detected using the substrate OPD at 490 nm absorbance.

In one example, after an enzyme-labeled second antibody directed against the first unlabeled antibody is washed from the immobilized phase, color or chemiluminiscence is developed and measured by incubating the immobilized capture reagent with a substrate of the enzyme. Then the amount of free VEGF concentration is calculated by comparing with the color or chemiluminescence generated by the standard VEGF run in parallel.

Kits

As a matter of convenience, the assay method of this invention can be provided in the form of a kit. Such a kit is a packaged combination including the basic elements of:

(a) capture reagents comprised of polyclonal and monoclonal antibodies against human VEGF molecule, wherein the monoclonal antibody binds specifically to the C-terminal of the VEGF molecule, in a weight ratio of about 0.8:1 to 1.2:1 of monoclonal to polyclonal antibody; and (b) detection reagents comprised of detectable (labeled or unlabeled) antibodies that bind to the KDR and FLT1 receptor binding domains of VEGF.

These basic elements are defined hereinabove.

Preferably, the kit further comprises a solid support for the capture reagents, which may be provided as a separate element or on which the capture reagents are already immobilized. Hence, the capture antibodies in the kit may be immobilized on a solid support, or they may be immobilized on such support that is included with the kit or provided separately from the kit. Preferably, the capture reagents are coated on a microtiter plate. The detection reagent may be labeled antibodies detected directly or unlabeled antibodies that are detected by labeled antibodies directed against the unlabeled antibodies raised in a different species. Where the label is an enzyme, the kit will ordinarily include substrates and cofactors required by the enzyme, and where the label is a fluorophore, a dye precursor that provides the detectable chromophore. Where the detection reagent is unlabeled, the kit may further comprise a detection means for the detectable antibodies, such as the labeled antibodies directed to the unlabeled antibodies, preferably in a fluorimetric-detected format.

In a preferred specific embodiment, the weight ratio of monoclonal antibody to polyclonal antibody in the kit is about 1:1, the detectable antibody is a biotinylated murine monoclonal antibody, the monoclonal antibody is murine or rat, more preferably murine, and most preferably MAb 3.5F8, the polyclonal antibody is affinity purified, and more preferably from goal or rabbit, most preferably rabbit, and the amount of murine monoclonal antibodies is 0.4 µg/ml and the amount of rabbit polyclonal antibodies is 0.4 µg/ml. Preferably, the capture reagents are immobilized in this kit. Also, preferably the detectable antibody is MAb A4.6.1.

The kit also typically contains instructions for carrying out the assay, and/or VEGF as an antigen standard (e.g., purified VEGF, preferably recombinantly produced VEGF), as well as other additives such as stabilizers, washing and incubation buffers, and the like.

Examples of standards for VEGF are recombinant human VEGF produced in mammalian cells available from Genentech, Inc., South San Francisco, Calif.

The components of the kit will be provided in predetermined ratios, with the relative amounts of the various reagents suitably varied to provide for concentrations in solution of the reagents that substantially maximize the sensitivity of the assay. Particularly, the reagents may be provided as dry powders, usually lyophilized, including excipients, which on dissolution will provide for a reagent solution having the appropriate concentration for combining with the sample to be tested.

The following examples are intended to illustrate one embodiment now known for practicing the invention, but the invention is not to be considered limited to these examples. All open and patented literature citations herein are expressly incorporated by reference.

EXAMPLE 1

2. Materials and Methods 2.1. Reagents

Purified recombinant human VEGF165 (rhVEGF) expressed in *Escherichia coli* (Genentech, South San Francisco, Calif.) was used as the standard and for the controls (prepared in ELISA diluent as defined below and stored at −70° C.). Streptavidin-β-galactosidase (Strep-β-gal) was purchased from Boehringer Mannheim, W. Gemany, MUG was purchased from Sigma, St. Louis, Mo. Dimethylsulfoxide (DMSO) was purchased from Sigma.

2.2. Antibodies to VEGF

Antibodies against rhVEGF165 were prepared as described in Kim et al., *Growth Factors*, 7:53 (1992). Briefly, BALB/c mice were hyperimmunized intraperitoneally with a 10 mg dose of rhVEGF165 conjugated to keyhole limpet hemocyanin. Spleen cells were fused with a mouse myeloma line and culture supernatants from wells containing hybridomas were screened for the presence of MAbs to rhVEGF165 by an ELISA. Positive hybridomas were cloned twice using the limiting dilution technique. The monoclonal antibodies used in this ELISA have been characterized in Kim et al, supra (1992). One of the capture antibodies, MAb 3.5F8, is thought to bind near the heparin binding domain, amino acid residues 111–165, with a $K_d$ of 13 pM. Rodriguez et al., supra (1998).

The rabbit polyclonal antibody (PAb) used as the other coat antibody was generated by injecting VEGF into a rabbit using a standard protocol, and purified by passing it through an affinity column to which VEGF was coupled to capture the polyclonal antibody, thus removing the immunoglobulins from the sample. The molecules that are not the desired antibody were washed off and the bound antibody was eluted with 0.2 M glycine, pH 2, then the pH was brought to neutral prior to dialysis overnight in PBS at 4° C., and the elutent containing the antibody was used for the multi-site assay.

The detection antibody, MAb A4.6.1, binds rhVEGF165 with a Kd of 86 pM. Several lines of evidence suggest that this MAb binds rhVEGF near the KDR receptor binding region (Kim et al, supra (1992)).

The hybridoma cell line capable of producing MAb 3.5F8 was deposited at the American Type Culture Collection (ATCC), 10801 University Boulevard, Manassas, Va., 20110-2209, on Jul. 3, 2001, and has been assigned ATCC accession number PTA-3499. The hybridoma cell line capable of producing MAb A4.6.1 was deposited at the ATCC (address above) on Mar. 29, 1991, and has been assigned ATCC accession number HB 10709. The deposits were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if a culture of the material(s) on deposit should die or be lost or destroyed when cultivated under suitable conditions, the material(s) will be promptly replaced on notification with another of the same. Availability of the deposited matexial(s) is not to be construed as a license to practice the invention in contravention of the rights granted under the authority of any government in accordance with its patent laws.

2.3. Biotinylation of MAb A4.6.1

The MAb A4.6.1 was biotinylated with biotinylamidocaproic acid-N-hydroxysuccinimide ester (Biotin-X-NHS) (Research Organics, Cleveland, Ohio) according to the following protocol. The MAb A4.6.1 was dialyzed against 100 mM $NaHCO_3$, pH 85 overnight at 2–8° C. A total of 60 $\mu$l of a 5-mg/ml solution of Biotin-X-NHS in DMSO was added to the MAb (adjusted after dialysis to a concentration of 2–10 mg/ml) using a 1:10 (w/w) ratio of Biotin MAb. This mixture was allowed to incubate for two hours at ambient temperature with gentle agitation, and the reaction was stopped by the addition of 5 $\mu$l of ethanolamine. After conjugation, the antibody was extensively dialyzed against PBS at 2–8° C. with gentle agitation and PBS changed every two hours for a total of three times.

2.4. Multi-Site VEGF ELISA

Two MAbs, 3.5F8 (coat) and biotinylated A4.6.1 (detection), and one PAb (coat) as described above were used to develop a specific and sensitive VEGF ELISA. In this ELISA, 100 $\mu$l/well each of MAb 3.5F8 and the affinity-purified PAb were mixed together and then added to MaxiSorp™ 96-well microtiter plates (Nunc, Roskilde, Denmark) at 0.4 $\mu$g/ml each in 0.05 M sodium carbonate, pH 9.6. Following 24–74-hour incubation at 2–8° C., the coated plates were washed 3 times with 400 $\mu$l ELISA wash buffer (PBS containing 0.05% TWEEN-20™ detergent) using a BIOTEK EL304™ platewasher (Biotek Instruments, Winooski, Vt.), and blocked with ELISA blocking diluent at 200 $\mu$l/well (PBS containing 0.5% BSA, 0.05% TWEEN-20™, and 0.05% PROCLIN™ 300 antibiotic, pH 7.2) for 1–3 hours at ambient temperature with agitation. After blocking, the plates were washed again 3 times with 400 $\mu$l ELISA wash buffer. Then, 100 $\mu$l/well of standards, samples, or controls were added to duplicate wells and incubated for 1.5–2 hours at 37° C. with agitation. For quantitation of rhVEGF165 in human plasma, the standard curve was prepared in ELISA diluent (PBS containing 0.5% BSA, 0.05% TWEEN-20™, 0.05% PROCLIN™ 300, 5 mM EDTA, and 0.35 M NaCl, pH 6.3±0.1). The standard curve was 128 pg/ml diluted serially 1:2 to 2 pg/ml. After the sample/standard incubation, the plates were washed six times with 400 $\mu$l ELISA wash buffer, and 100 $\mu$l/well of MAb A4.6.1-Biotin, freshly diluted 1:200 to its optimal concentration in ELISA diluent, was added to the plates.

After a 1.5–2-hour incubation at 37° C. with agitation, the plates were washed six times as described above and 100 μl/well of strep-β-gal, diluted 1:40K in ELISA diluent, was added to the plates. After a 45–60-minute incubation at 37° C. with agitation, the plates were washed 6 times as described above and 100 μl/well of MUG/DMSO (1/100), freshly diluted to 340 μg/ml in a solution of 0.1 M NaPO$_4$, containing 1 mM MgCl$_2$ at pH 7.3±0.1, was added to the plates. The substrate reaction incubated for 15–17 hours at 37° C. with agitation in the dark (plate was wrapped with foil). The reaction was stopped by adding 150 μl/well of 0.15 M glycine, pH 10.5±0.1. The fluorescent unit (FSU) of the well contents was read on a CYTOFLUOR 4000™ fluorescent plate reader (PerSeptive Biosystems, Framingham, Mass.) using 360 nm excitation and 460 nm emission filters. A four-parameter curve fit program was used to generate a standard curve, from which sample and control concentrations were interpolated. FSU readings were stable for at least 30 minutes at room temperature after 150 μl glycine was added.

2.5. Human Plasma Samples

The ability to accurately measure VEGF in human plasma was assessed using several approaches. The effect of plasma on the assay sensitivity and performance was evaluated using rhVEGF165. Known amounts of rhVEGF165 were added to individual human plasma samples and the percent recovery determined as follows: (1) the amount of endogenous VEGF in the sample, determined from a parallel sample, was subtracted from the total amount of VEGF measured in the sample, (2) the 'recovered' VEGF value was then divided by the amount of VEGF added to the sample and multiplied by 100. The dilution linearity of rhVEGF165 added into individual human plasmas was also evaluated. In these studies, following rhVEGF165 addition, each plasma sample was diluted 1:10 in ELISA diluent followed by serial 1:2 dilutions in ELISA diluent. High and low matrix (standard) controls were prepared in neat human EDTA plasma (frozen). They were diluted 1/10 in ELISA diluent for a final concentration of 10% plasma.

Endogenous VEGF levels were measured in individual human plasma samples. Blood from normal healthy individuals was drawn into 15% K3 EDTA Vacutainer tubes (Becton Dickenson, San Jose, Calif.). The tubes were centrifuged at 2000×g for 20 min and the plasma was collected. Plasma samples were diluted 1:10 in ELISA diluent for use in the assay. The dilution linearity of endogenous VEGF in selected samples was also evaluated as described above.

3. Results 3.1 Sample Stability

The stability of neat human EDTA plasma was examined for three freeze-and thaw cycles. The plasma received a dry ice treatment followed by a gentle mixing in warm water in order to thaw. The data in Table 1 below demonstrate that there is no significant effect of quantitation of VEGF following freeze-and thaw treatments. Therefore, human EDTA plasma is stable for three freeze-and thaw cycles.

TABLE 1

Net Freeze-Thaw Stability of Normal Human EDTA Plasma

| hu EDTA Plasma | Two-Site | Multi-Site | |
|---|---|---|---|
| 32 | 22.11 | 78.84 | Fresh |
|  | 25.4 | 75.16 | 1 freeze-thaw |
|  | 14.85 | 75.16 | 2 freeze-thaw |
|  | 18.88 | 72.08 | 3 freeze-thaw |
| mean | 20.31 | 75.31 |  |

TABLE 1-continued

Net Freeze-Thaw Stability of Normal Human EDTA Plasma

| hu EDTA Plasma | Two-Site | Multi-Site | |
|---|---|---|---|
| stddev |  | 4.51 | 2.77 |
| % CV |  | 2.2 | 4 |
| 33 | 35.44 | 100.24 | Fresh |
|  | 35.87 | 101.71 | 1 freeze-thaw |
|  | 35.44 | 101.71 | 2 freeze-thaw |
|  | 39.19 | 101.71 | 3 freeze-thaw |
| mean | 36.49 | 101.34 |  |
| stddev | 1.81 | 0.73 |  |
| % CV | 5 | 1 |  |
| 34 | 17.51 | 78.18 | Fresh |
|  | 25.03 | 94.6 | 1 freeze-thaw |
|  | 22.11 | 94.6 | 2 freeze-thaw |
|  | 24.72 | 83.95 | 3 freeze-thaw |
| mean | 22.34 | 87.83 |  |
| stddev | 3.48 | 8.16 |  |
| % CV | 16 | 9 |  |
| 39 | 29.35 | 84.62 | Fresh |
|  | 31.11 | 81.39 | 1 freeze-thaw |
|  | 28.02 | 75.16 | 2 freeze-thaw |
|  | 31.11 | 71.51 | 3 freeze-thaw |
| mean | 29.90 | 78.17 |  |
| stddev | 1.50 | 5.93 |  |
| % CV | 5 | 8 |  |
| 38 | 23.43 | 83.95 | Fresh |
|  | 29.94 | 80.07 | 1 freeze-thaw |
|  | 21.8 | 83.95 | 2 freeze-thaw |
|  | 24.72 | 66.84 | 3 freeze-thaw |
| mean | 24.97 | 78.70 |  |
| stddev | 3.52 | 8.12 |  |
| % CV | 14 | 10 |  |
| Mean | 12 | 6 |  | stddev = standard deviation
CV = coefficients of variation 3.2 Limit of Detection Approximately 20 replicates of the blank, 1, 2, 4 and 8 pg/ml standard, were assayed in the multi-site VEGF ELISA herein. The limit of detection was determined by the analyte (VEGF) concentration for which the measured mean FSU response minus two standard deviations was greater than the mean FSU response plus two standard deviations of the blank fluorescence emission (460 nm). Results in Table 2 show that the limit of detection is 8 pg/ml in ELISA diluent. Since plasma samples are typically diluted 1:10 to minimize matrix interference, as little as 80 pg/ml, or 1.6 pM VEGF can be measured in the original sample

TABLE 2

Limit of Detection (0.4 μg/ml, 0.4 μg/ml)

| replicates | std 0 pg/ml FSUs | std 1 pg/ml FSUs | std 2 pg/ml FSUs | std 4 pg/ml FSUs | std 8 pg/ml FSUs |
|---|---|---|---|---|---|
| 1 | 1103 | 1277 | 1351 | 1546 | 2216 |
| 2 | 1091 | 1382 | 1359 | 1617 | 2292 |
| 3 | 1103 | 1336 | 1413 | 1745 | 2241 |
| 4 | 1180 | 1328 | 1986 | 1770 | 2266 |
| 5 | 1235 | 1321 | 1382 | 1654 | 2216 |
| 6 | 1135 | 1382 | 1631 | 1735 | 2216 |
| 7 | 1180 | 1306 | 1328 | 1692 | 2266 |
| 8 | 1154 | 1125 | 1512 | 1654 | 2241 |
| 9 | 1079 | 1351 | 1366 | 1682 | 2279 |
| 10 | 1129 | 1559 | 1529 | 1678 | 2384 |
| 11 | 1129 | 1314 | 1445 | 1654 | 2266 |
| 12 | 1263 | 1413 | 1299 | 1617 | 2228 |
| 13 | 1079 | 1382 | 1336 | 1631 | 2216 |
| 14 | 1235 | 1284 | 1851 | 1716 | 2565 |
| 15 | 1135 | — | 1711 | 1780 | 2266 |

TABLE 2-continued

Limit of Detection (0.4 µg/ml, 0.4 µg/ml)

| replicates | std 0 pg/ml FSUs | std 1 pg/ml FSUs | std 2 pg/ml FSUs | std 4 pg/ml FSUs | std 8 pg/ml FSUs |
|---|---|---|---|---|---|
| 16 | 1129 | — | 1590 | 2077 | 2266 |
| 17 | 1017 | — | 1445 | 1654 | 2279 |
| 18 | 1351 | — | 1445 | 1740 | 2371 |
| 19 | 1079 | — | 1546 | 1599 | 2318 |
| 20 | 2025 | — | 1626 | 1663 | 2228 |
| mean | 1192 | 1340 | 1508 | 1695 | 2281 |
| std. dev. | 211 | 94 | 183 | 108 | 82 |
| +1 SD | 1402 | 1434 | 1690 | 1803 | 2363 |
| +2 SD | 1613 | 1528 | 1873 | 1911 | 2445 |
| −1 SD | 981 | 1246 | 1325 | 1587 | 2199 |
| −2 SD | 770 | 1152 | 1142 | 1479 | 2117 |

3.3 Testing and Preparation of Anti-VEGF PAb

Two different preparations of rabbit polyclonal antibody against rhVEGF purified from the same rabbit but a different bleed were compared in the assay, using MAb 3.5F8 as the monoclonal antibody, and using 0.4 µg/ml of each type of antibody. The results, indicated in FIG. 1, show that both antibodies are suitable for use.

Figure 2:
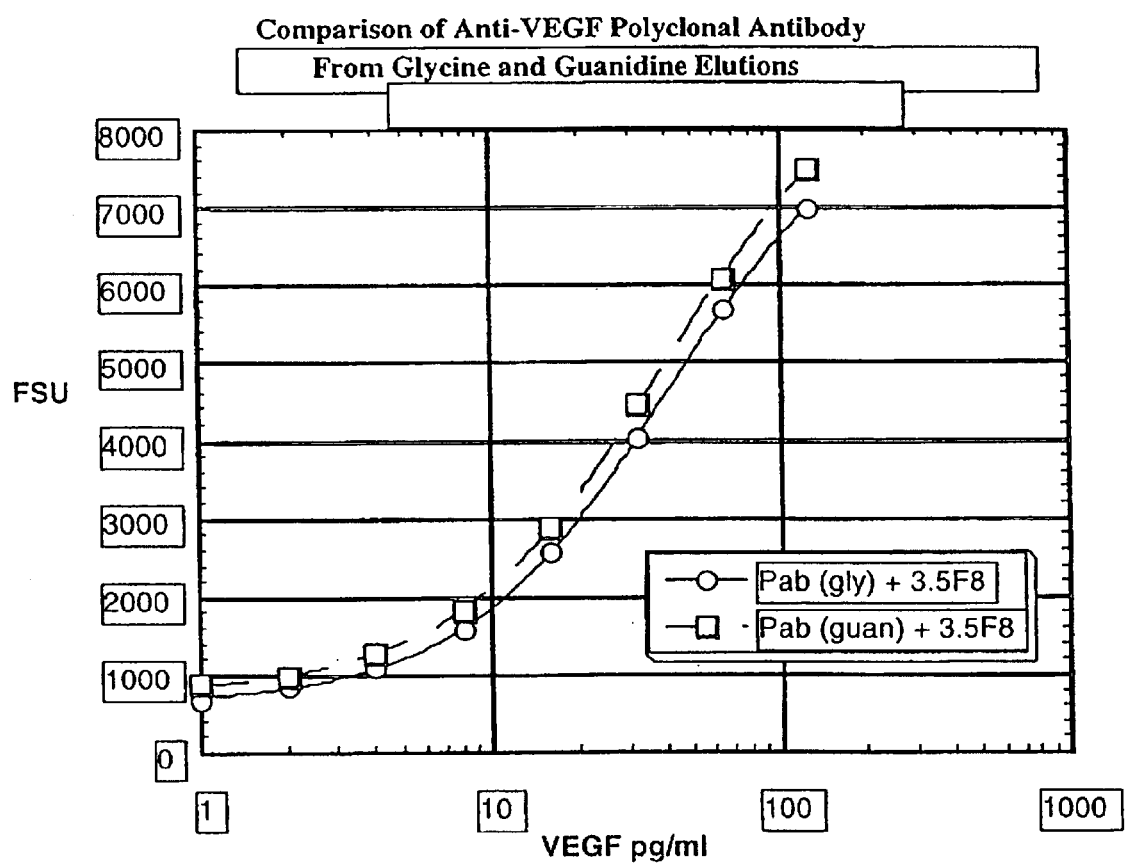
FIG. 2 shows a comparison of ELISAs herein using guanidine versus glycine elution of the affinity-purified rabbit polygonal antibody against VEGF.

Rabbit polyclonal antibody elution was performed with glycine followed by guanidine and the resulting antibodies were used in the assay with the preferred conditions herein. Results in FIG. 2 and Table 3 show that there is no significant difference between the two elution methods. However, the glycine elution seems to be slightly more sensitive. Comparison of normal human EDTA plasma samples as well as the High and Low Matrix controls show similar quantitation in both preparations. The guanidine peak is more tightly bound to the VEGF than the glycine peak.

TABLE 3

Comparison of glycine and guanidine as eluents

| Normal Human EDTA Plasma | PAb (Glycine) + Mabs 3.5 F8/A4.6.1 (pg/ml) | PAb (Guanidine) + MAbs 3.5F8/A4.6.1 (pg/ml) | % Recovery |
|---|---|---|---|
| 1 | 37 | 48 | 77 |
| 2 | 41 | 34 | 123 |
| 3 | 112 | 90 | 124 |
| 4 | 79 | 62 | 128 |
| 5 | 49 | 36 | 136 |
| 6 | 40 | 57 | 71 |
| 7 | 59 | 45 | 132 |
| 8 | 35 | 31 | 116 |
| High Mat | 99 | 102 | 97 |
| Low Mat | 9 | 8 | 115 |
| | | Mean % Recovery | 112 |

3.4 Robustness/Ruggedness

Inter-assay and intra-assay precision was evaluated for the low and high matrix controls by ANOVA statistical analysis. Matrix controls were prepared by spiking rhVEGF into neat human EDTA plasma at low and high concentrations to fall within the assay range. Results show that the inter-assay variability (CV) ranges from 11–17% while the intra-assay variability ranges from 8–14%. The data is summarized in Table 4.

TABLE 4

Reproducibility of the Matrix Controls

| Assay Name | High (pg/ml) | Low (pg/ml) |
|---|---|---|
| kn324p2 | 107.5 | 6.8 |
| kn324p2 | 111.2 | 11.6 |
| kn324P3 | 93.8 | 10.4 |
| kn324p3 | 96.7 | 11.2 |
| kn320p7 | 103.6 | 13.7 |
| kn320p7 | 103.6 | 13.7 |
| kn320p8 | 99.7 | 14.3 |
| kn320p8 | 102.0 | 14.7 |
| kn322p2 | 110.6 | 13.3 |
| kn322p2 | 102.0 | — |
| kn322p3 | 97.0 | 14.4 |
| kn322p3 | 103.9 | 13.9 |
| kn322p1 | 99.0 | 12.0 |
| kn322p1 | 95.2 | 12.3 |
| kn320p3 | 101.1 | 15.3 |
| kn320p3 | 98.0 | 14.5 |
| kn320p2 | 105.1 | 14.9 |
| kn320p2 | 100.5 | 14.2 |
| kn320p1 | 106.0 | 14.1 |
| kn320p1 | 103.4 | 13.9 |
| kn319p2 | 87.1 | 10.2 |
| kn319p2 | 100.2 | 9.3 |
| kn319p1 | 97.6 | 9.4 |
| kn319p1 | 99.6 | 9.1 |
| kn316p1 | 92.4 | 11.7 |
| kn316p1 | 97.9 | 11.3 |
| kn313p1 | 117.8 | 18.8 |
| kn313p1 | 111.4 | 16.2 |
| kn212p2 | 92.4 | 14.6 |
| kn212p2 | 92.4 | 15.7 |
| kn311p1 | 123.9 | 14.2 |
| kn212p1 | 103.8 | 13.9 |
| kn212p1 | 93.2 | 13.7 |
| kn331p1 | 106.2 | 12.9 |
| kn331p1 | 109.2 | 13.3 |
| kn331p2 | 99.8 | 11.9 |
| Matrix Controls | Intra-assay (% CV) | Inter-assay (% CV) |
| Low | 14.0 | 11.0 |
| High | 8.0 | 17.0 |

3.5 Hook Effect

Figure 3:
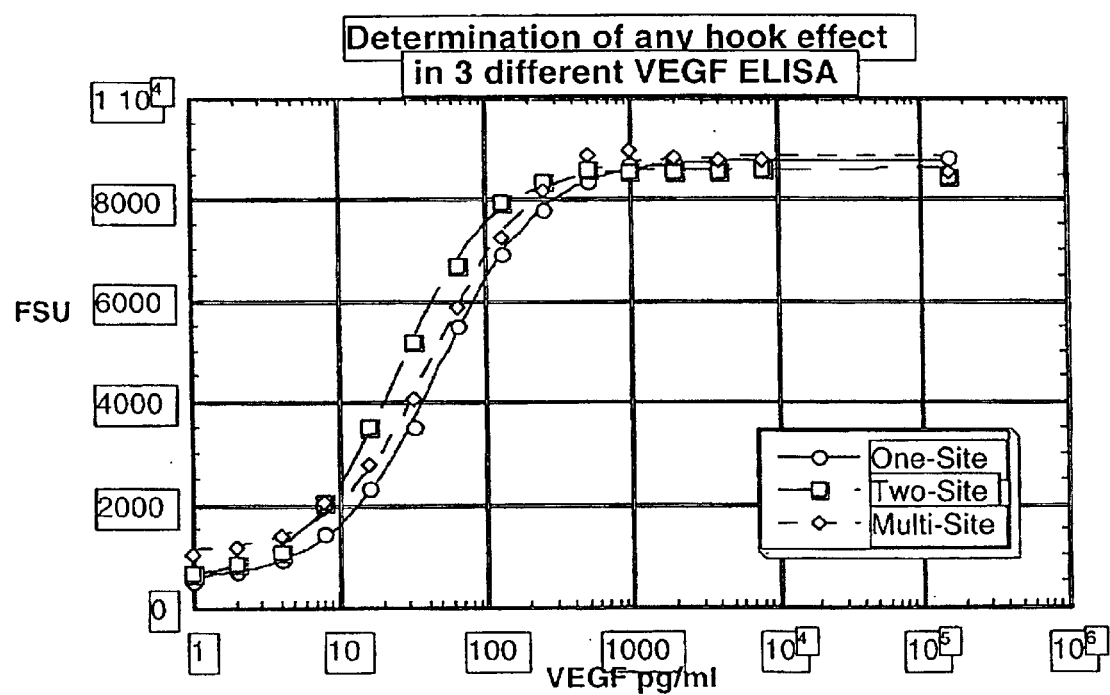
FIG. 3 shows a comparison of typical standard curves for, and possible hook effect of, three different VEGF ELISAs, wherein the circles show the one-site assay with MAb 3.5F8 alone as coat and detection agent, the squares show the two-site assay with MAb 3.5F8 as coat and MAb A4.6.1 as detection agent, and the diamonds show the multi-site assay herein with MAb 3.5F8 and an affinity-purified polyclonal antibody as coat and MAb A4.6.1 as detection agent.

Several samples in the past have shown non-linearity of increasing VEGF measured with increasing sample dilution. Therefore, the multi-site ELISA herein was tested for a hook effect (side-by-side comparison with the one- and two-site ELISAs). rhVEGF was diluted from 16 ng/ml to 1 pg/ml in assay buffer. Results (depicted in FIG. 3) show that there is no significant drop in VEGF quantitation. However, a slight drop and plateauing effect can be seen from 512 pg/ml onward. Since the sample dilutions used in the multi-site ELISA assay herein give rise to concentrations less than 128 pg/ml, the hook effect is not a concern.

3.6 Coat Maximization

Figure 4:
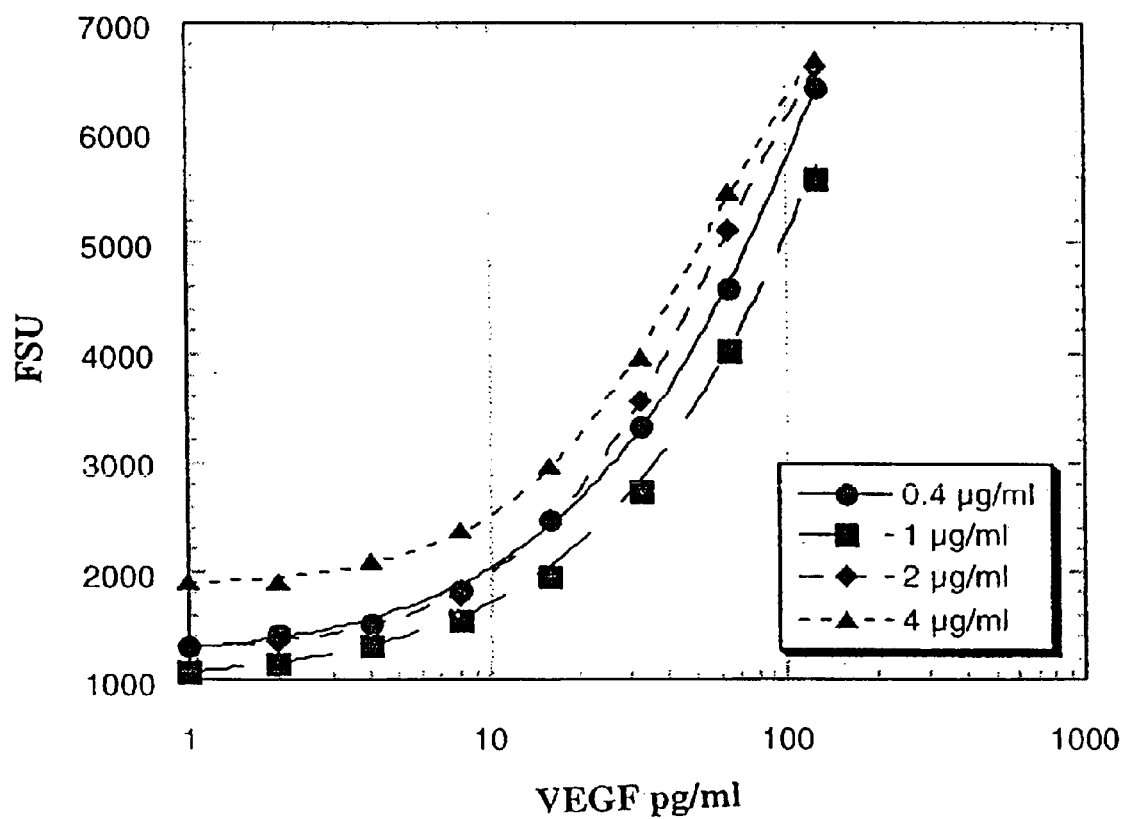
FIG. 4 shows monoclonal antibody MAb 3.5F8 coat maximization wherein the ELISA uses 0.4 (circles), 1 (squares), 2 (diamonds), or 4 (triangles) μg/ml monoclonal antibody and 1 μg/ml affinity-purified polyclonal antibody.
Figure 5:
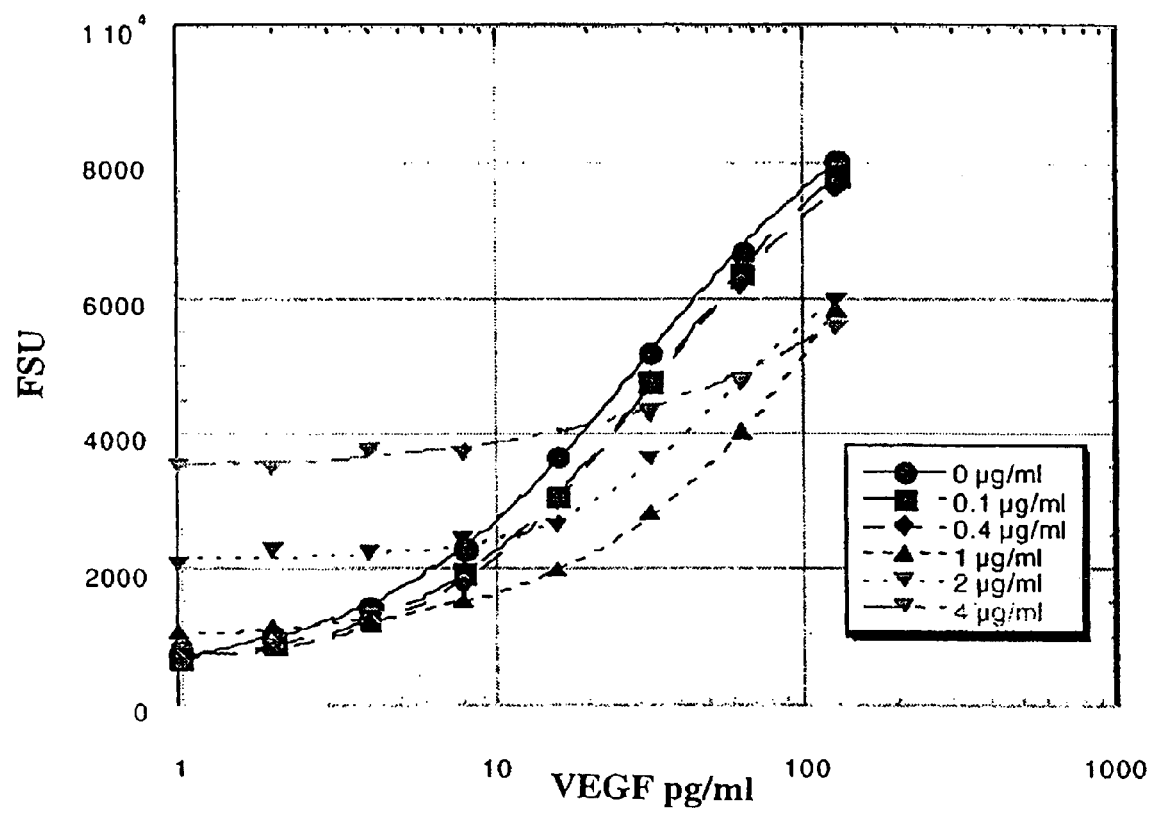
FIG. 5 shows rabbit polyclonal antibody coat maximization wherein the ELISA uses 0 (circles), 0.1 (squares), 0.4 (diamonds), 1 (triangles), 2 (reverse triangles with dotted lines), or 4 (reverse triangles with solid lines) μg/ml affinity-purified polyclonal antibody and 0.4 μg/ml MAb 3.5F8.

The procedures for determining coat maximization were the same as described above in the Methods section except that the concentration of either the PAb or the MAb 3.5F8 coat was varied. Specifically, for FIG. 4 the concentration of MAb 3.5F8 was varied from 0.4 to 4 µg/ml while keeping constant the concentration of polyclonal antibody (at 1 µg/ml), and for FIG. 5 and Table 5 the concentration of polyclonal antibody was varied from 0.4 to 4 µg/ml while keeping constant the concentration of MAb 3.5F8 (at 0.4 µg/ml).

While the 0.1 and 0.4 µg/ml concentrations of MAb 3.5F8 and of the PAb at the constant concentration of the other coat antibody were essentially the same in VEGF quantitation for the low and high control, the upper limit of coat concentration (e.g., 0.4 µg/ml) is preferred to better the chances that the VEGF is captured. While the concentration of 1 µg/ml of MAb 3.5F8 and PAb increased the amount of VEGF measured in each case, such a concentration also gave higher background. Hence, the results show that the preferred concentrations for both capture reagents is about 0.4 µg/ml.

TABLE 5

Coat Maximization of the Polyclonal Antibody plus MAb 3.5F8

| MAb 3.5F8 | 0.4 µg/ml | 0.4 µg/ml | 0.4 µg/ml | 0.4 µg/ml |
|---|---|---|---|---|
| PAb | 1 µg/ml | 0.4 µg/ml | 0.1 µg/ml | 0 |
| High matrix (pg/ml): | 100.4 | 89.3 | 94.0 | 97.3 |
| Low matrix (pg/ml): | 22.4 | 9.7 | 10.1 | 5.4 |
| | | | | ° |
| Eight separate | 97.3 | 33.5 | 42.5 | 10.7 |
| normal human | 202.5 | 106.5 | 77.0 | 19.7 |
| plasma donors | 162.3 | 52.9 | 59.0 | 26.8 |
| (pg/ml): | 92.0 | 27.5 | 29.8 | 11.1 |
| | 115.6 | 41.4 | 42.5 | 11.0 |
| | 202.5 | 70.8 | 69.7 | 15.8 |
| | 409.9 | 196.6 | 207.9 | 94.9 |
| | 512.1 | 25.7 | 275.0 | 113.0 |

3.7 pH Profile of the Multi-site VEGF ELISA

A pH profile was performed to determine whether changing pH of the assay buffer would increase or decrease recovery of VEGF in normal human EDTA plasma. Changing the pH could dissociate binding proteins or other complexes, if any, which would interfere with the MAb A4.6.1 detection.

The procedure for examining the pH profile of the assay was the same as described in the Methods section above except that for the sample incubation and biotin incubation, the assay buffer was adjusted using NaOH or HCl, resulting in assay buffers ranging from pH 4 to 9 A standard curve, a low and high matrix, and four normal human EDTA plasma samples were evaluated from dilutions performed using these varying-pH assay buffers.

Figure 6:
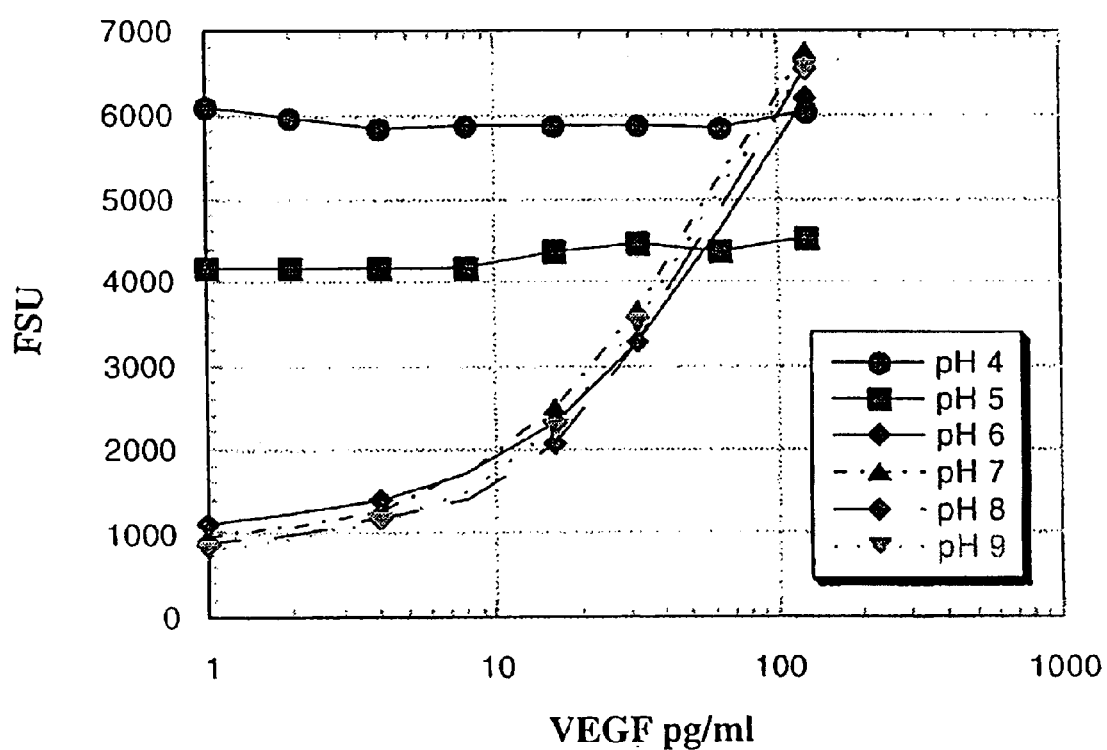
FIG. 6 shows the effect of pH on the multi-site VEGF ELISA herein, wherein the circles represent the ELISA at pH 4, the squares, pH 5, the diamonds, pH 6, the triangles, pH 7, the half-line diamonds, pH 8, and the reverse diamonds, pH 9.

Results in FIG. 6 and Table 6 show that there was no recovery of VEGF at pH 4 and 5. However, pH 6–9 revealed good VEGF plasma recovery with the assay control within an acceptable range. There was no significant difference in VEGF quantitation as a consequence of varying the pH of the assay buffer from 6 to 9. However, the preferred assay buffer is one with a pH of about 6.35±0.1, which results in maximal VEGF binding and is appropriate for all dilution steps of the assay.

TABLE 6

VEGF Recovery Normal Human EDTA Plasma at varying pH

| pH Normal Human EDTA Plasma | 4 | 5 | 6 pg/ml | 7 pg/ml | 8 pg/ml | 9 pg/ml |
|---|---|---|---|---|---|---|
| 1 | — | — | 198.9 | 122.0 | 173 3 | 204.0 |
| 2 | — | — | 141 4 | 81.7 | 138.7 | 138.6 |
| 3 | — | — | 240.7 | 150.3 | 220.9 | 243.5 |
| 4 | — | — | 112.2 | 113.2 | 176.7 | 190.3 |
| Controls | | | | | | |
| High Matrix | — | — | 104.5 | 105.1 | 93.8 | 124.0 |
| Low Matrix | — | — | 25.7 | 25.1 | 19.7 | 16.9 |

3.8 Dilution Linearity

Figure 7:
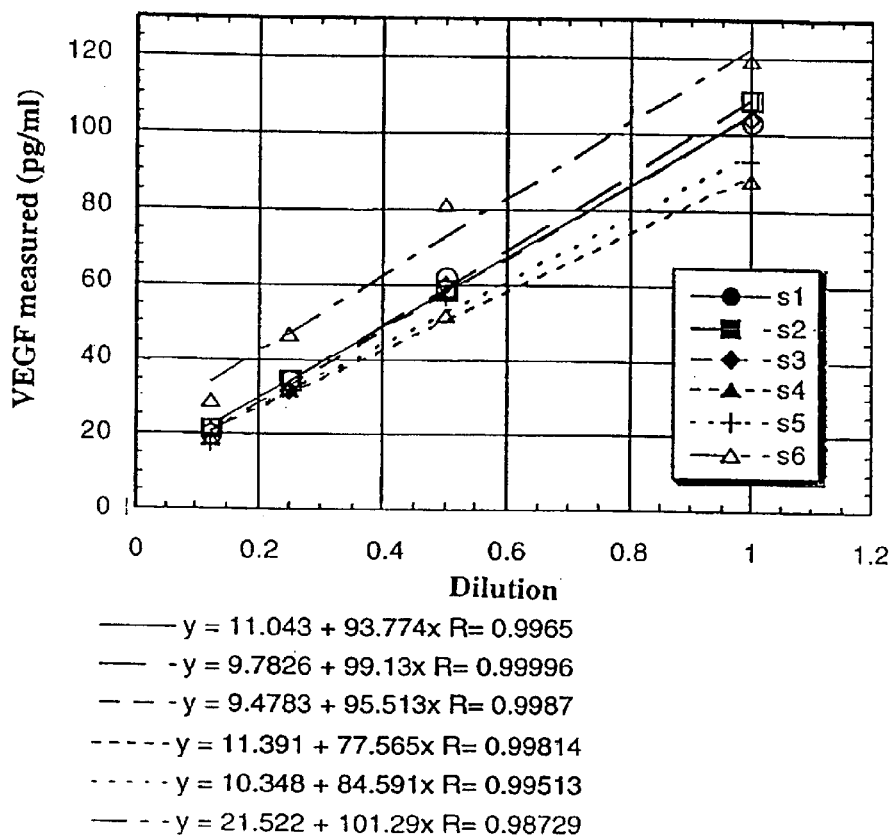
FIG. 7 shows dilution linearity of six normal human EDTA plasma samples spiked with rhVEGF in the multi-site VEGF ELISA.

Approximately 85 pg/ml rhVEGF was spiked into neat human EDTA plasma and serially diluted to 1/10, 1/20, 1/40, and 1/80 and analyzed. The results, in Table 7 and FIG. 7, show that rhVEGF spiked in EDTA plasma showed linear correlation to expected concentration, with a coefficient correlation of 0.996. The percent difference between dilution-corrected concentration values determined for successive serial dilutions did not exceed a mean of 19%+7.5, as shown in Table 7.

TABLE 7

Dilution Linearity of Normal Human EDTA Plasma

| Normal Human EDTA Plasma (samples) | [Measured] pg/ml | Dilution | Corrected Concentration | % Difference |
|---|---|---|---|---|
| S1 | 103 | 10 | 1026 | — |
| | 62 | 20 | 1237 | 21 |
| | 35 | 40 | 1416 | 14 |
| | 20 | 80 | 1599 | 13 |
| S2 | 109 | 10 | 1088 | — |
| | 59 | 20 | 1176 | 8 |
| | 35 | 40 | 1416 | 20 |
| | 22 | 80 | 1788 | 26 |
| S3 | 104 | 10 | 1039 | — |
| | 60 | 20 | 1202 | 16 |
| | 32 | 40 | 1278 | 6 |
| | 21 | 80 | 1677 | 31 |
| S4 | 88 | 10 | 878 | — |
| | 52 | 20 | 1036 | 18 |
| | 32 | 40 | 1278 | 23 |
| | 19 | 80 | 1528 | 20 |
| S5 | | 10 | 926 | — |
| | 93 | 20 | 1136 | 23 |
| | 57 | 40 | 1278 | 12 |
| | 32 | 80 | 1433 | 12 |
| S6 | 18 | 10 | 1192 | — |
| | 119 | 20 | 1612 | 35 |
| | 81 | 40 | 1893 | 17 |
| | 47 | 80 | 2298 | 21 |
| | 29 | | | |

3.9 Accuracy—Quantitation of VEGF in Human Plasma

Endogenous VEGF levels were measured in freshly-collected plasma from several normal healthy individuals The individual human EDTA plasma samples were spiked with lowest, low, mid, and high concentrations of rhVEGF so as to fall within the assay range of the standard curve Endogenous VEGF concentrations were determined and subtracted from the measured concentration to obtain comparison to the targeted spike. Results in Table 8 show that mean % recoveries were 99%, 113%, 106%, and 118% for the high, mid, low, and lower spikes, respectively.

TABLE 8

Spike Recovery of rhVEGF in Human EDTA Plasma

|  | [Endogenous] pg/ml | [Measured] pg/ml | [Measured-Endogenous] pg/ml | [Targeted] pg/ml | % Recovery |
|---|---|---|---|---|---|
| High Spike | 18.6 | 100.5 | 81.9 | 85.3 | 96 |
|  | 22.5 | 114.8 | 92.3 | 85.3 | 108 |
|  | 30.3 | 111.0 | 80.8 | 85.3 | 95 |
|  | 22.8 | 96.2 | 73.4 | 85.3 | 86 |
|  | 18.4 | 103.2 | 84.9 | 85.3 | 100 |
|  | 34.1 | 121.1 | 87.0 | 85.3 | 102 |
| Mean % Recovery |  |  |  |  | 99 |
| Mid Spike | 21.0 | 98.3 | 47.1 | 49.3 | 96 |
|  | 9.1 | 89.1 | 80.1 | 49.3 | 162 |
|  | 10.8 | 66.8 | 55.9 | 49.3 | 113 |
|  | 21.0 | 59.5 | 38.5 | 49.3 | 78 |
|  | 9.1 | 66.8 | 57.8 | 49.3 | 117 |
| Mean % Recovery |  |  |  |  | 113 |
| Low Spike | 4.5 | 32.9 | 28.4 | 22.9 | 124 |
|  | 10.0 | 32.9 | 22.9 | 22.9 | 100 |
|  | 14.9 | 38.3 | 23.4 | 22.9 | 102 |
|  | 8.6 | 31.2 | 22.6 | 22.9 | 99 |
|  | 9.3 | 33.7 | 24.4 | 22.9 | 107 |
|  | 15.9 | 40.9 | 25.0 | 23.5 | 106 |
|  | 36.2 | 58.8 | 22.6 | 23.5 | 96 |
|  | 38.9 | 66.4 | 27.5 | 23.5 | 117 |
| Mean % Recovery |  |  |  |  | 106 |
| Lower Spike * | 4.3 | 24.9 | 20.2 | 17.8 | 114 |
|  | 4.6 | 26.1 | 21.5 | 17.8 | 120 |
|  | 7.4 | 27.9 | 20.4 | 17.8 | 114 |
|  | 6.6 | 26.4 | 19.9 | 17.8 | 111 |
|  | 10.8 | 33.1 | 22.2 | 17.8 | 124 |
|  | 5.5 | 29.6 | 24.0 | 17.8 | 135 |
|  | 3.9 | 22.7 | 18.6 | 17.8 | 105 |
| Mean % Recovery |  |  |  |  | 118 |

*0.4 µg/ml MAb 3.5F8 + 0.4 µg/ml PAb coat 3.10 Accuracy—Quantitation of VEGF in Normal Rat EDTA Plasma An individual and two pooled male rat EDTA plasma samples were spiked with low, mid and high concentration of rhVEGF so as to fall within the assay range of the standard curve. Endogenous VEGF concentrations were determined and subtracted from the measured concentration in order to obtain comparison to the targeted spike (dilution control). Spikes were then diluted 1:2 in ELISA diluent to determine dilution linearity. Results in Table 9 show that mean percent recoveries range from 84–103% for the high, mid and low spikes that were greater than 6.25 pg/ml.

TABLE 9

VEGF Spike Recovery in Normal Rat EDTA Plasma

| [Expected] Dilution Control pg/ml | [Measured] Male rat Pool 1 pg/ml | % Recovery | [Measured] Male rat Pool 2 pg/ml | % Recovery | [Measured] Individual Male rat pg/ml | % Recovery | Mean % Recovery |
|---|---|---|---|---|---|---|---|
| High spike |  |  |  |  |  |  |  |
| 151 | 160 | 106 | 155 | 103 | 148 | 98 | 103 |
| 98 | 106 | 109 | 85 | 87 | 92 | 95 | 97 |
| 53 | 58 | 109 | 43 | 81 | 43 | 82 | 91 |
| 24 | 25 | 105 | 15 | 61 | 18 | 76 | 81 |
| Mid spike |  |  |  |  |  |  |  |
| 44 | 41 | 94 | 40 | 92 | 39 | 89 | 92 |
| 22 | 27 | 125 | 20 | 93 | 16 | 71 | 96 |
| 11 | 13 | 115 | 7 | 66 | 7 | 65 | 82 |
| 5 | 5 | 104 | 0 | 0 | 1 | 15 | 40 |

TABLE 9-continued

VEGF Spike Recovery in Normal Rat EDTA Plasma

| [Expected] | [Measured] | | [Measured] | | [Measured] | | |
| --- | --- | --- | --- | --- | --- | --- | --- |
| Dilution Control pg/ml | Male rat Pool 1 pg/ml | % Recovery | Male rat Pool 2 pg/ml | % Recovery | Individual Male rat pg/ml | % Recovery | Mean % Recovery |
| Low spike | | | | | | | |
| 20 | 18 | 88 | 19 | 93 | 12 | 62 | 81 |
| 10 | 14 | 135 | 9 | 86 | 6 | 63 | 95 |
| 6 | 6 | 102 | 1 | 18 | 0 | 0 | 40 |
| 3 | 2 | 52 | 0 | 0 | 0 | — | 26 |
| Lower spike | | | | | | | |
| 10 | 10 | 98 | 8 | 76 | 5 | 49 | 74 |
| 5 | 8 | 149 | 3 | 47 | 2 | 42 | 79 |
| 4 | 8 | 202 | 0 | 0 | 0 | 0 | 67 |
| Endogenous | LTS | | 43 | | 39 | | |

3.11 Linearity of Normal Rat EDTA Plasma in ELISA Diluent

Figure 8A:
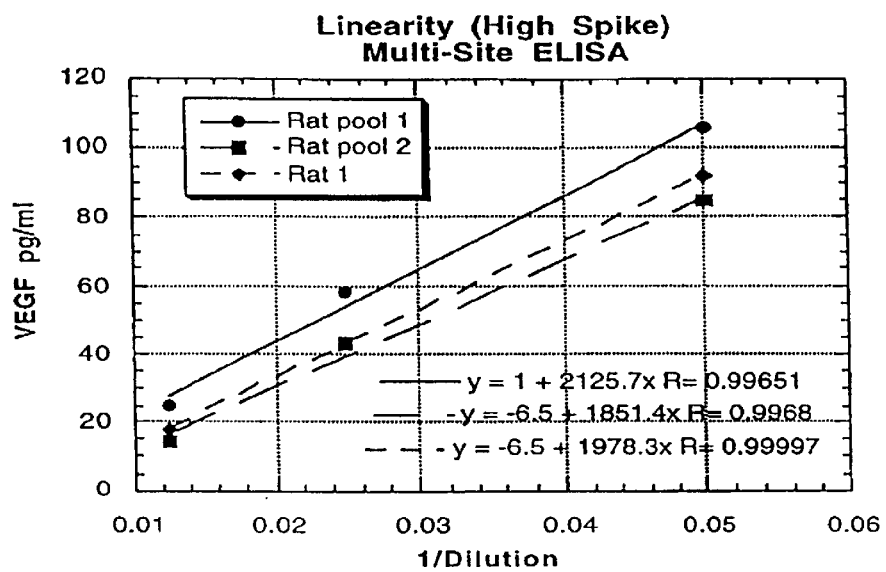
Figure 8B:
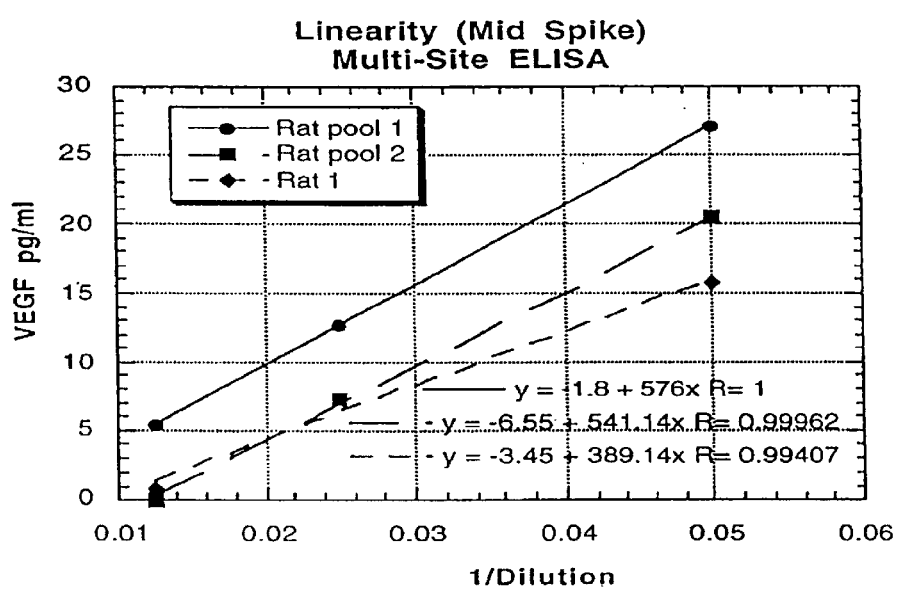
Figure 8C:
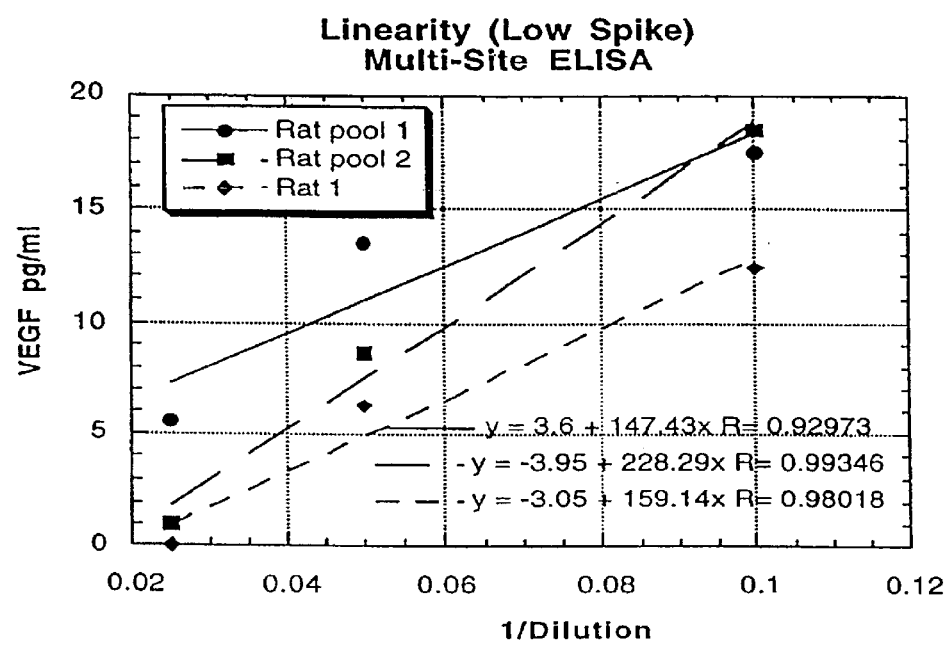

Rat EDTA plasma (2 male pools, 1 individual) was tested for linearity of dilution. Neat plasma samples were spiked with low (20 pg/ml), mid (44 pg/ml), and high (98 pg/ml) concentrations of rhVEGF and were serially diluted 1/10, 1/20, 1/40, 1/80 in ELISA diluent. Results in Table 10 and FIGS. 8A–8C show that normal rat plasma samples dilute linearly following a minimum 1/20 dilution in the assay range of 8–128 pg/ml

TABLE 10

Summary of Linearity for Rat Plasma Samples (in units of coefficient of correlation (R))

| Spike | Rat pool 1 | Rat pool 2 | Rat 1 | Mean R value |
| --- | --- | --- | --- | --- |
| High | 0.996 | 0.996 | 0.999 | 0.997 |
| Mid | 1 | 0.999 | 0.994 | 0.998 |
| Low | 0.929 | 0.993 | 0.98 | 0.967 |

3.12 Accuracy—Quantitation of VEGF in Normal Yorkshire Pig EDTA Plasma

Figure 9A:
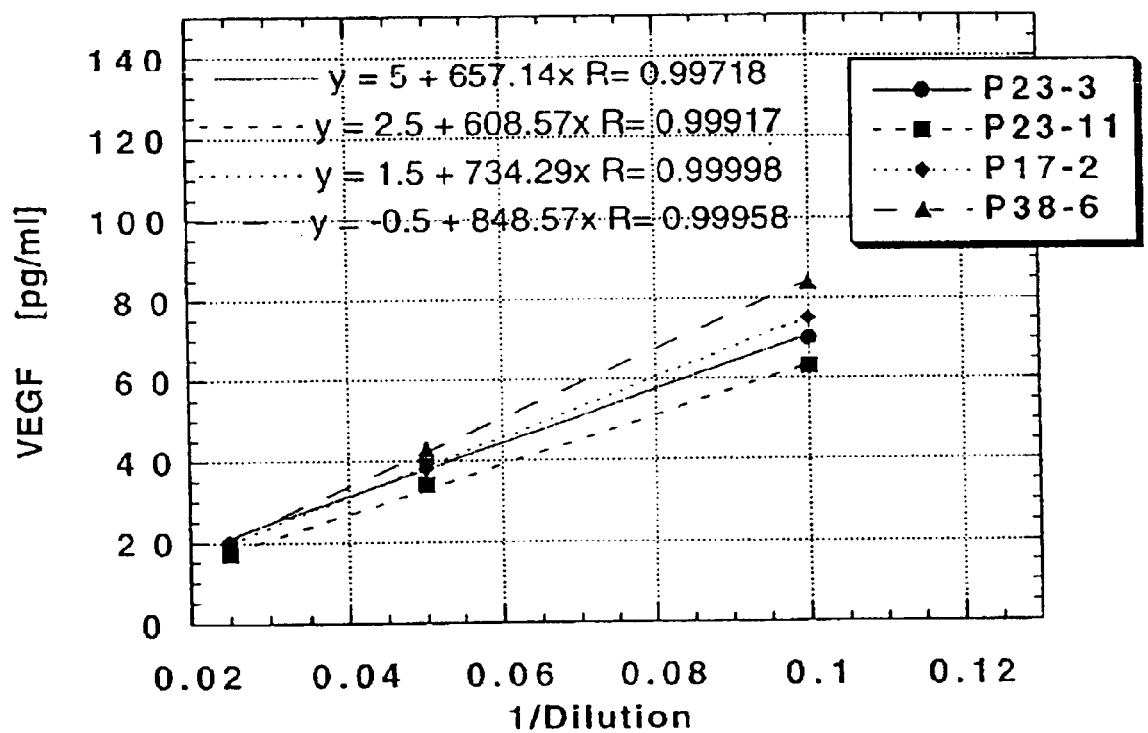
FIGS. 9A–9B show linearity of, respectively, four female and four male Yorkshire pig EDTA plasma samples spiked with rhVEGF.
Figure 9B:
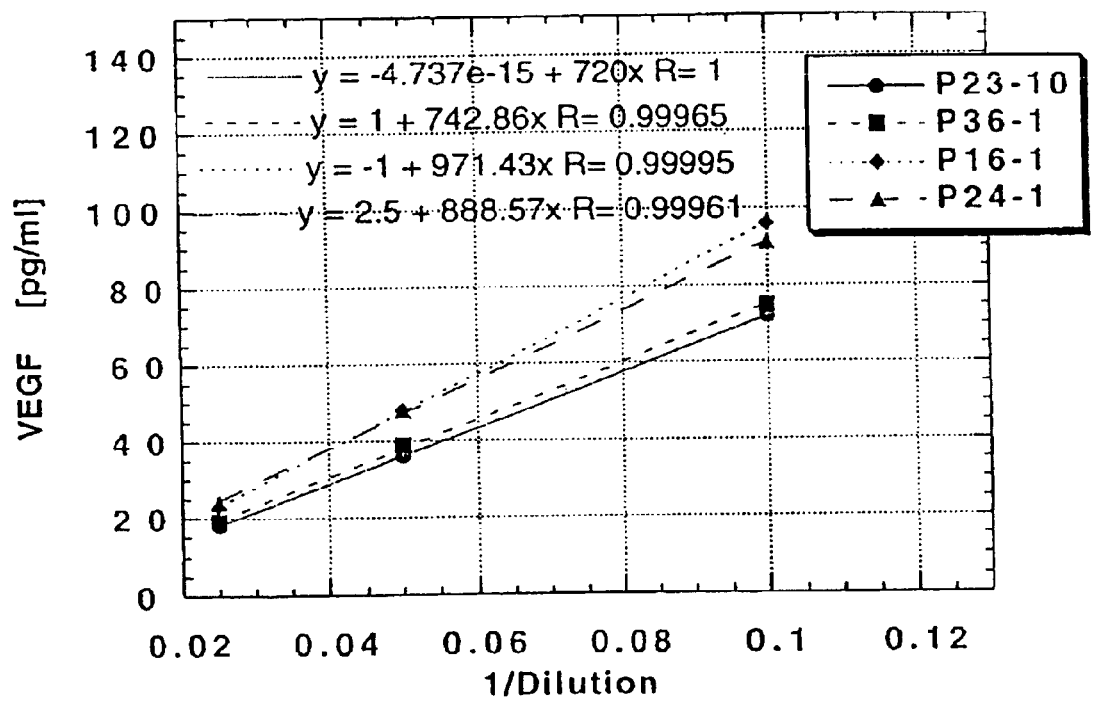

Eight Yorkshire pig EDTA plasma samples (four males and four females) were spiked with low, mid, and high concentrations of rhVEGF so as to fall within the assay range of the standard curve. Endogenous VEGF concentrations were determined and subtracted from the measured concentration in order to obtain comparison to the targeted spike (dilution control). Spikes were then diluted 1/10, 1/20, 1/40, 1/80 in ELISA diluent to determine dilution linearity. Results, shown in FIG. 9A (females) and FIG. 9B (males), and in Table 11, show that normal rat plasma samples dilute linearly following a minimum 1/20 dilution in the assay range of 8–128 pg/ml

TABLE 11

Summary of Linearity for Yorkshire Pig Samples

| Gender | Coefficient of Correlation (R) |
| --- | --- |
| Female | 0.99718 |
| Female | 0.99917 |
| Female | 0.99998 |
| Female | 0.99958 |
| Male | 1 |

TABLE 11-continued

Summary of Linearity for Yorkshire Pig Samples

| Gender | Coefficient of Correlation (R) |
| --- | --- |
| Male | 0.99965 |
| Male | 0.99995 |
| Male | 0.99961 |
| mean | 0.99939 |
| s.d. | 0.00093491 |
| % CV | 0.094 |

3.13 Detection of Various Forms of VEGF Using Three ELISAs

Figure 10A:
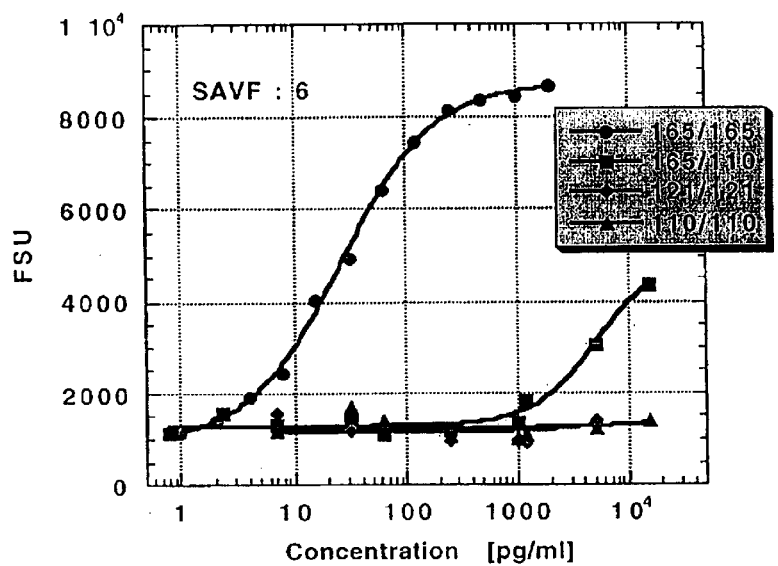
FIGS. 10A–10C show the specificity of three different ELISA assays for VEGF forms 165/165 (circles), 165/110 (squares), 121/121 (diamonds), and 110/110 (triangles).
Figure 10B:
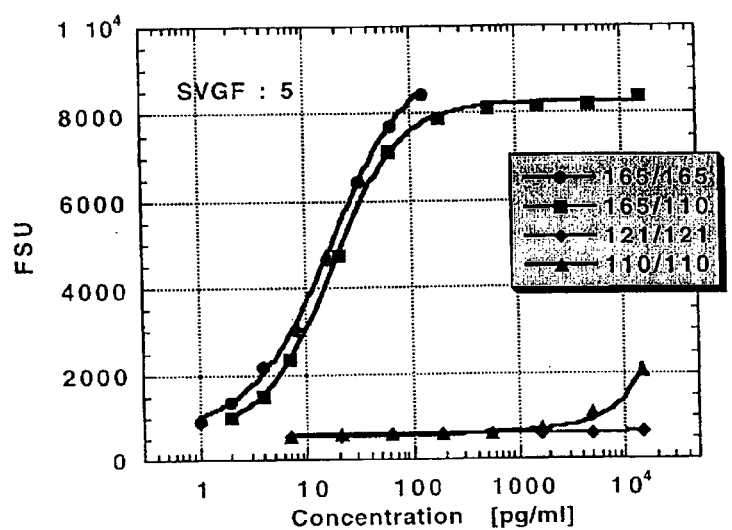
Figure 10C:
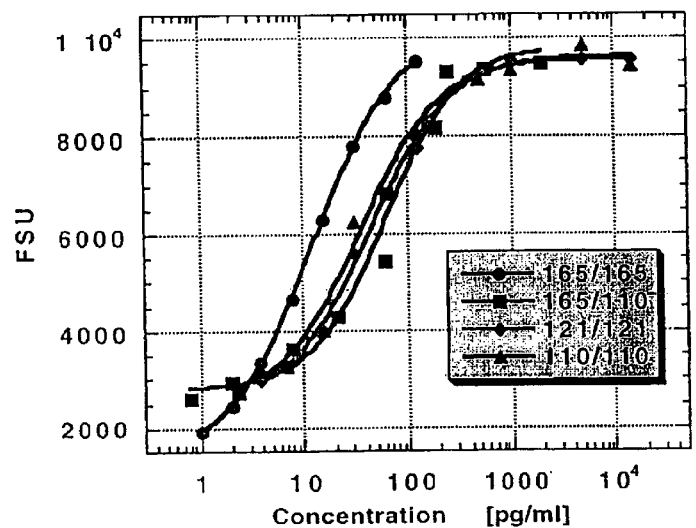

This experiment was designed to determine if the multi-site ELISA herein could measure all the variants of VEGF. FIGS. 10A, 10B, and 10C show a comparison of the single-site, two-site, and multi-site ELISAs for VEGF, respectively. It can be seen by comparing these graphs that the multi-site assay herein is capable of capturing more VEGF variants.

3.14 Detection Using Two-Site, Multi-Site, or PAb as Coat

The multi-site ELISA herein using PAb and MAb 3.5F8 as coat antibodies was compared to an ELISA using only MAb 3.5F8 or PAb as coat antibody for evaluating the amount of VEGF in normal human samples. The results, set forth in Table 12, show that the amount of VEGF detected in pg/ml was much higher for the multi-site assay than for the assay with PAb alone or MAb 3.5F8 alone.

TABLE 12

Amount of VEGF in Normal Human Plasma Samples Using PAb Alone, MAb alone, or PAb and MAb

| | Capture Reagent | | |
| --- | --- | --- | --- |
| NHP Sample # | MAb 3.5F8 (Mean pg/ml) | PAb to VEGF (Mean pg/ml) | PAb to VEGF + MAb 3.5F8 (Mean pg/ml) |
| 1 | 49 | 173 | 225 |
| 2 | 26 | LTS | 149 |
| 3 | 39 | 124 | 211 |
| 4 | 41 | 103 | 189 |
| 5 | 27 | LTS | 153 |
| 6 | 29 | LTS | 149 |
| 7 | 16 | LTS | 159 |

TABLE 12-continued

Amount of VEGF in Normal Human Plasma Samples Using PAb Alone, MAb alone, or PAb and MAb

| | Capture Reagent | | |
|---|---|---|---|
| NHP Sample # | MAb 3.5F8 (Mean pg/ml) | PAb to VEGF (Mean pg/ml) | PAb to VEGF + MAb 3.5F8 (Mean pg/ml) |
| 8 | 25 | LTS | 144 |
| 9 | 21 | LTS | 122 |
| 10 | 36 | 148 | 185 |
| 11 | 24 | 72 | 171 |
| 12 | 23 | LTS | 145 |
| 13 | 40 | 103 | 200 |
| 14 | 34 | 83 | 143 |
| 15 | 42 | LTS | 200 |
| 16 | 20 | 85 | 152 |
| 17 | 51 | 196 | 285 |
| 18 | 25 | LTS | 145 |
| 19 | 20 | LTS | 154 |
| 20 | 20 | LTS | 143 |
| 21 | 23 | LTS | 155 |
| 22 | 28 | 77 | 163 |
| 23 | 39 | 180 | 285 |
| 24 | 24 | 87 | 168 |
| 25 | 45 | 148 | 261 |
| 26 | 21 | 131 | 179 |
| 27 | 34 | LTS | 189 |
| 28 | 18 | LTS | 131 |
| 29 | 50 | 159 | 251 |
| 30 | 73 | LTS | 359 |
| 31 | 21 | 85 | 149 |
| 32 | 42 | 214 | 237 |
| 33 | 33 | LTS | 234 |
| 34 | 30 | 152 | 206 |
| 35 | 21 | 87 | 154 |
| 36 | 76 | 307 | 445 |
| 37 | 28 | 70 | 225 |
| 38 | 53 | 51 | 304 |
| 39 | 32 | 84 | 193 |
| 40 | 28 | LTS | 106 |
| 41 | 44 | 105 | 275 |
| 42 | 32 | 44 | 217 |
| 43 | 28 | 69 | 197 |
| 44 | 25 | LTS | 69 |
| 45 | 50 | 114 | 285 |
| 46 | 28 | 38 | 176 |
| 47 | 21 | 67 | 125 |
| 48 | 28 | 27 | 192 |
| 49 | 29 | LTS | 159 |
| 50 | 18 | 27 | 107 |

Figure 11A:
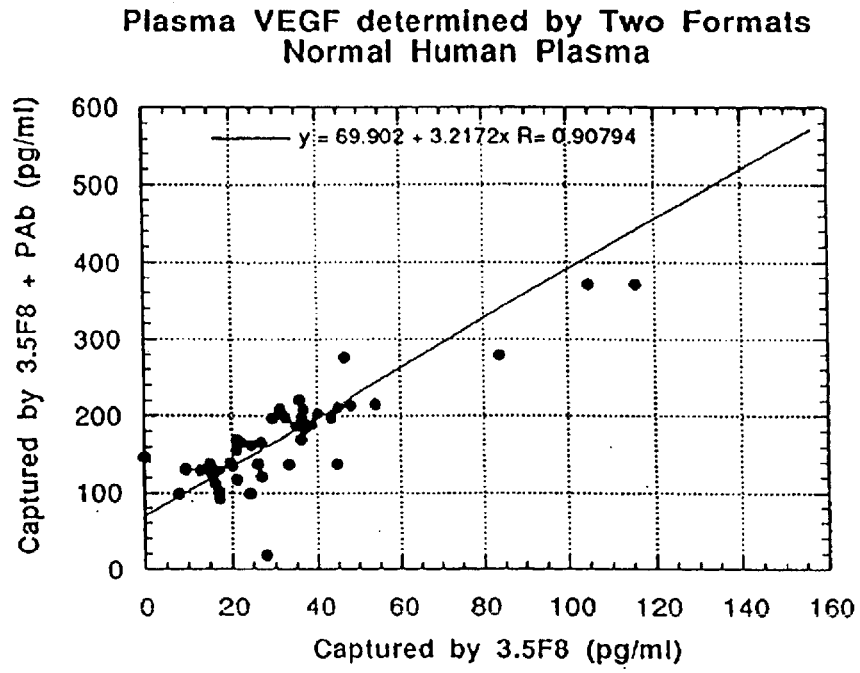
FIGS. 11A and 11B show, respectively, normal human plasma and serum VEGF detected by a two-site ELISA using only MAb 3.5F8 as coat reagent and by the multi-site ELISA herein using both the PAb and MAb 3.5F8 as coat reagents.
Figure 11B:
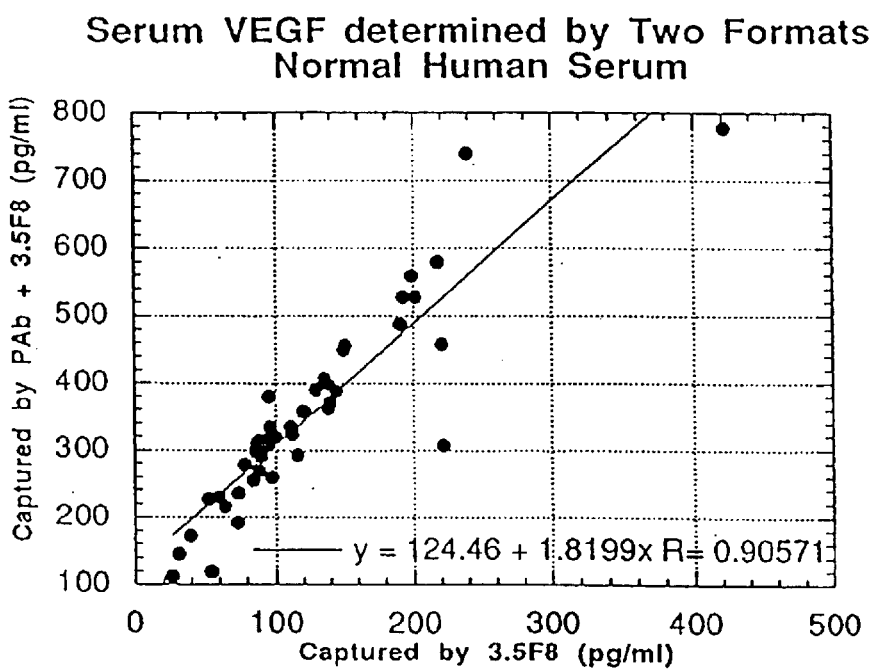

LTS = not detectable 3.15 Comparison of VEGF Levels in Normal Human Plasma and Normal Human Serum Using Two-Site and Multi-Site ELISAs Plasma and serum samples from normal human donors were analyzed by the two-site ELISA with MAb 3.5F8 as capture antibody and MAb A4.6.1 as detection antibody and by the multi-site assay herein using the PAb and MAbs and procedures noted in the Methods. The results, summarized in FIGS. 11A and 11B for plasma and serum respectively, indicate that the multi-site assay herein detects more VEGF in both types of samples than the two-site assay.

Figure 12:
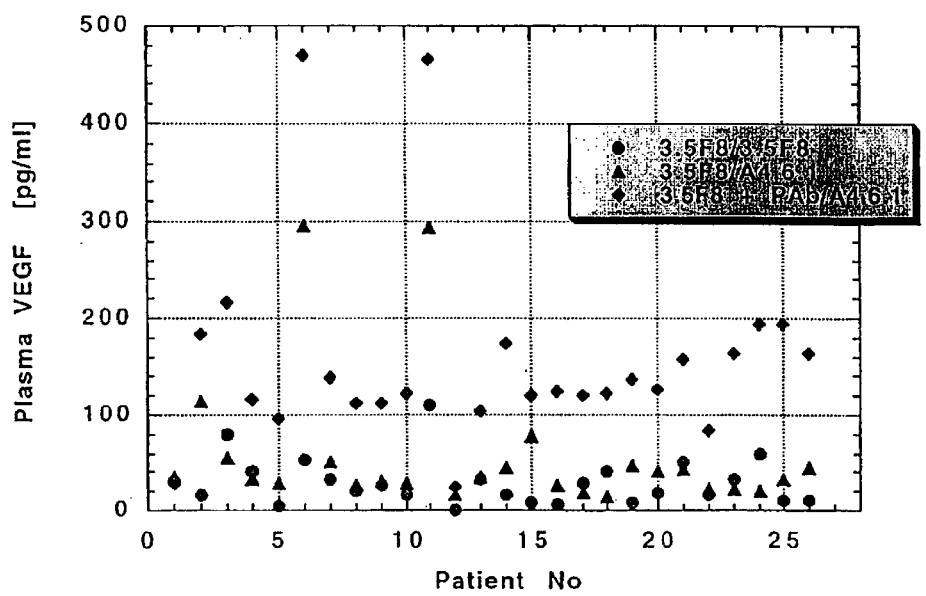
FIG. 12 shows the amounts of plasma VEGF in cardiac patients using all three assays described in the legend to FIG. 10, where the circles represent the single-site assay, the squares represent the two-site assay, and the triangles represent the multi-site assay.
Figure 13:
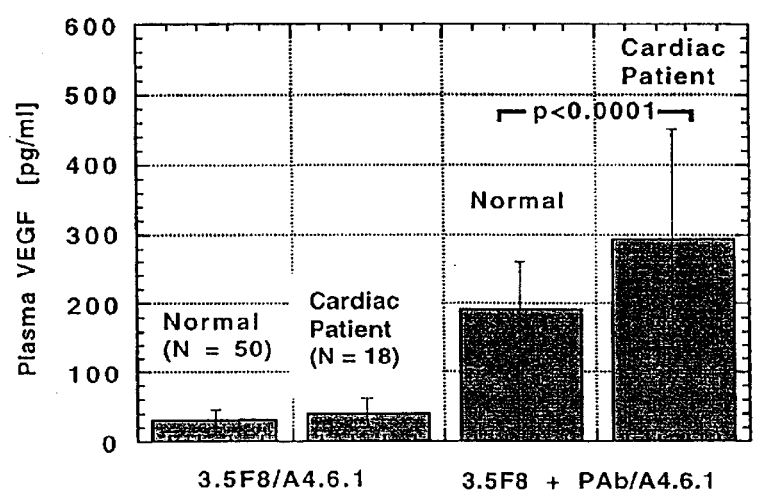
FIG. 13 shows plasma VEGF levels in normal donors and cardiovascular patients using the two-site assay with MAb 3.5F8 as coat and MAb A4.6.1 as detection antibody or the multi-site assay herein using MAb 3.5F8 and affinity-purified polyclonal antibody as coat and MAb A4.6.1 as detection antibody, where N is the number of patients.

3.16 Comparison of VEGF Levels in Normal and Cardio-pathological Patients Using Single-Site, Two-Site, and Multi-Site ELISAs Samples from normal human donors and from donors with cardiac disease who were enrolled in clinical trials sponsored by Genentech, Inc. to evaluate efficacy of TNK, a t-PA variant, were analyzed by the single-site ELISA with MAb 3.5F8 as coat and detection agent, by the two-site ELISA with MAb 3.5F8 as capture antibody and MAb A4.6.1 as detection antibody, and by the multi-site assay herein using the PAb and MAbs and procedures noted in the Methods. FIG. 12 shows the amounts of plasma VEGF in cardiac patients using all three assays, and FIG. 13 and Table 13 summarize the amounts of VEGF in normal and cardiac patients using the two-site and multi-site assays by the mean amount of VEGF, standard deviation, % CV and s.e.m. The results indicate that the multi-site assay herein detects more VEGF in both types of samples than the two-site assay.

TABLE 13

Sensitivity of Two-Site and Multi-Site Assays to VEGF in Normal and Cardiac Patients

| | Normal Donors | | Cardiac Patients | |
|---|---|---|---|---|
| | Two-site | Multi-site | Two-site | Multi-site |
| mean pg/ml | 32.61 | 192.40 | 37.54 | 279.23 |
| s.d. | 13.05 | 67.66 | 23.89 | 156.69 |
| % CV | 40.02 | 35.17 | 63.65 | 56.11 |
| s.e.m (Standard error mean) | 1.84 | 9.56 | 5.34 | 35 |

Figure 14:
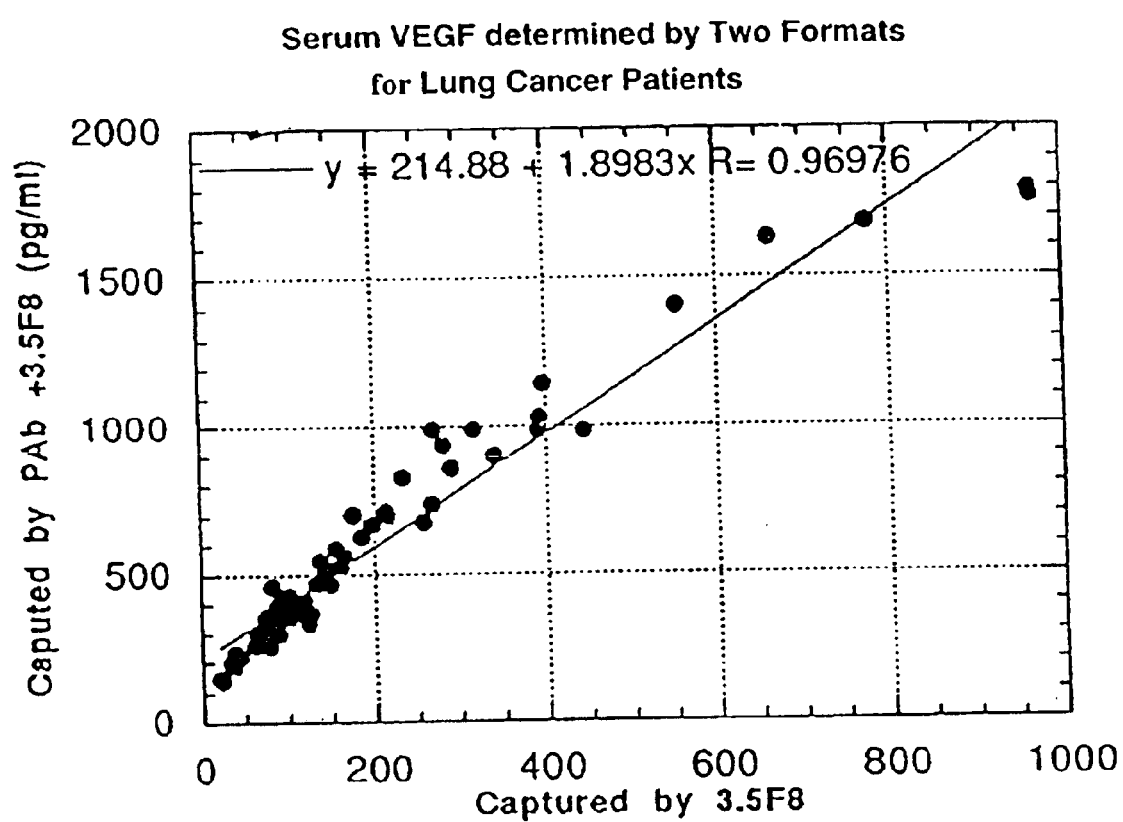
FIG. 14 shows serum VEGF from lung cancer patients detected by a two-site ELISA using only MAb 3.5F8 as coat reagent and by the multi-site ELISA herein using both the PAb and MAb 3.5F8 as coat reagents.

3.17 Comparison of Serum VEGF Levels in Lung Cancer Patients Using Two-Site and Multi-Site ELISAs Serum samples from non-small cell lung carcinoma patients were analyzed by the two-site ELISA with MAb 3.5F8 as capture antibody and MAb A4.6.1 as detection antibody and by the multi-site assay herein using the PAb and MAbs and procedures noted in the Methods. The results, shown in FIG. 14, indicate that the multi-site assay herein detects more VEGF in lung cancer samples than the two-site assay.

3.18 Levels of Serum VEGF in Diabetic Patients

Figure 15:
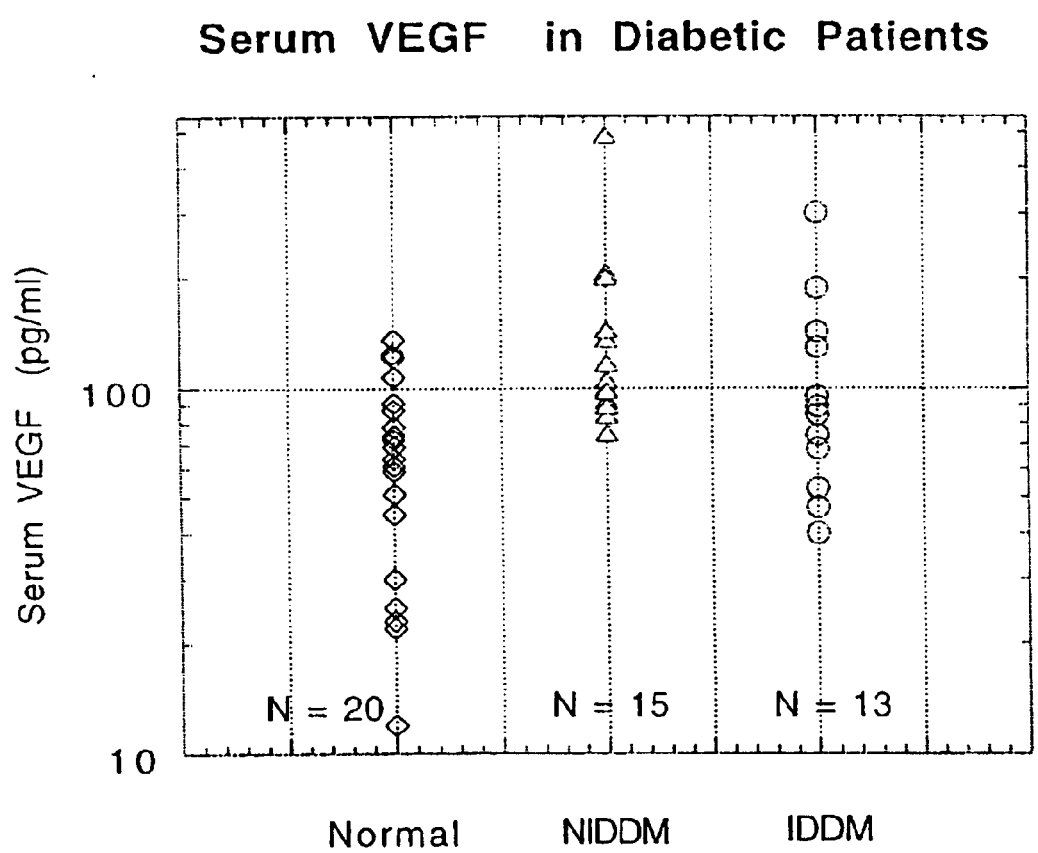
FIG. 15 shows serum VEGF levels in normal donors and diabetic patients (non-insulin-dependent diabetes mellitus (NIDDM) and insulin-dependent diabetes mellitus (IDDM)) using the two-site ELISA with MAb 3.5F8 as coat and MAb A4.6.1 as detection antibody.

Serum VEGF levels in normal humans and in patients with NIDDM (Type I diabetes) and IDDM (Type II diabetes) were measured using the two-site ELISA (MAb 3.5F8 as coat and MAb A4.6.1 as detection agent) described above. FIG. 15 shows that the levels of serum VEGF in NIDDM and IDDM patients were higher than in normal patients using this assay. Since the multi-site assay detects more VEGF than the two-site assay in other diseased patients, it would be expected that the multi-site assay herein would be suitable for detecting elevated levels of VEGF in diabetic patients.

3.19 Specificity of PAb to VEGF Versus PAb to DNase in Multi-Site Assay

Figure 16A:
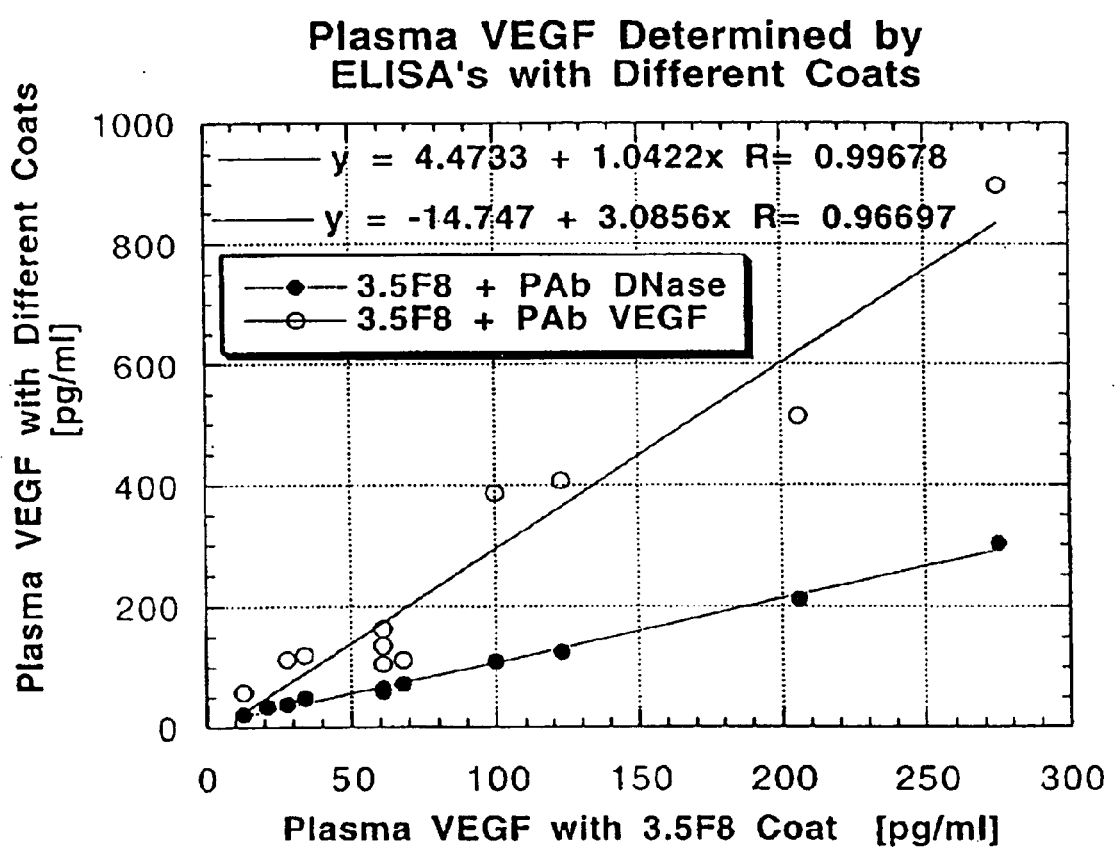
FIGS. 16A and 16B show graphs comparing an affinity-purified polyclonal antibody to DNase and an affinity-purified polyclonal antibody to VEGF as one of the coat reagents in the multi-site assay herein, as compared to the two-site assay using MAb 3.5F8 as coat reagent for human plasma.
Figure 16B:
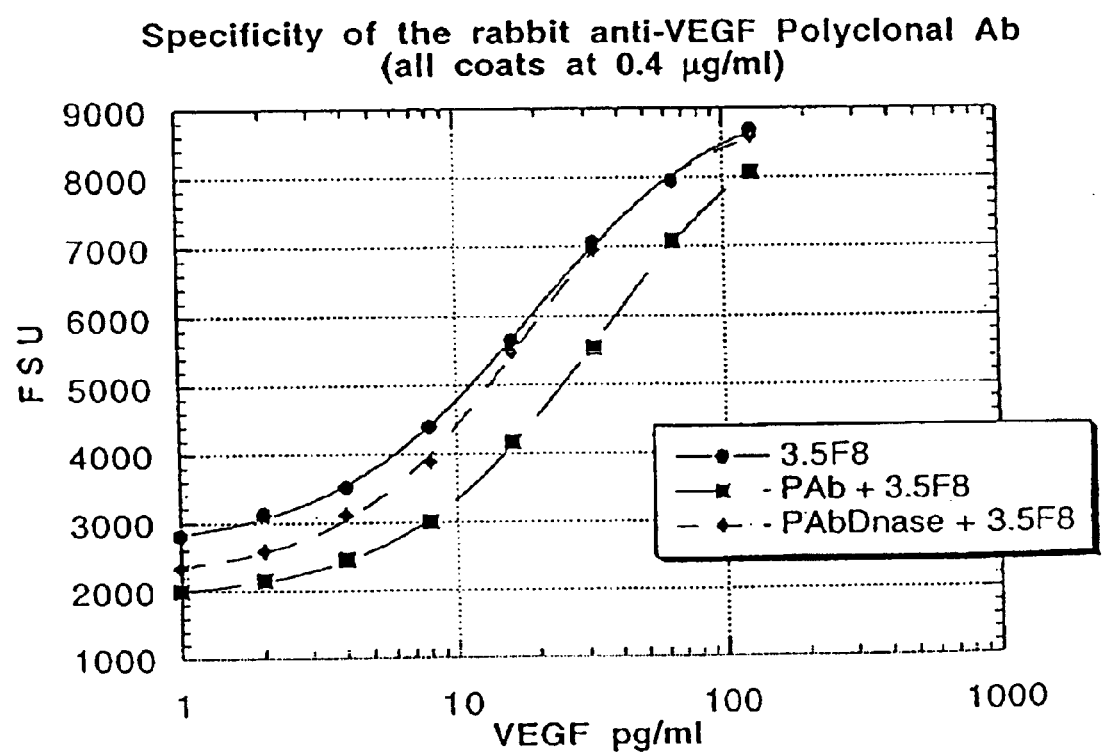

The two-site and multi-site ELISAs were carried out as described above for normal human plasma samples. In addition, a multi-site was carried out using PAb to DNase rather than PAb to VEGF as coat reagent. All were at the 0.4 μg/ml concentration. FIG. 16 and Table 14 show that the VEGF detected by multi-site VEGF assay is specific. Results from the ELISA using PAb to DNase plus MAb 3.5F8 show almost identical results as the ELISA using MAb 3.5F8 alone as capture reagent, with a slope of 1.04 (FIG. 16A).

TABLE 14

Human EDTA Plasma Evaluated for VEGF Amounts

| Human EDTA plasma | MAb 3.5F8 (0.4 µg/ml) | PAb to VEGF (0.4 µg/ml) and MAb 3.5F8 (0.4 µg/ml) | PAb to DNase (0.4 µg/ml) and MAb 3.5F8 (0.4 µg/ml) |
|---|---|---|---|
| High matrix (pg/ml): | 147.9 | 147.4 | 119.2 |
| Low matrix (pg/ml): | 12.8 | 18.3 | 12.5 |
| Seven separate normal human plasma donors | 61.1 | 164.0 | 59.5 |
| | 33.8 | 120.4 | 48.5 |
| (pg/ml): | 34.6 | 174.3 | 64.5 |
| | 47.4 | 104.5 | 102.1 |
| | 28.3 | 70.4 | 79.6 |
| | 67.6 | 113.0 | 71.8 |
| | 61.1 | 105.9 | 65.4 |

3.20 Summary of Preferred Assay and Results

| | |
|---|---|
| TYPE OF ASSAY | Immunoassay (Fluorimetric ELISA): mixture of a murine anti-VEGF monoclonal antibody (MAb 3.5F8) and a rabbit affinity-purified polyclonal antibody for capture and an anti-VEGF monoclonal antibody (MAb A4.6.1) for detection. |
| STANDARD | rhVEGF Reference Material VEGF or equivalent. Standard curve will be diluted in ELISA diluent: PBS/0.5%BSA/0.05%Polysorbate20/0.05% PROCLIN ™ 300/5 mM EDTA/0.35M NaCl, pH 6.35 ± 0.1 |
| SPECIES QUALIFIED | Human, Rat, Yorkshire Pig |
| BIOLOGICAL MATRIX | Serum, EDTA Plasma, ELISA diluent = Dilution buffer |
| ASSAY RANGE | 1–128 pg/ml in ELISA diluent |
| QUANTITATIVE RANGE IN BIOLOGICAL MATRIX | 80 pg/ml to 1280 pg/ml for human serum and EDTA plasma (1/10 minimum dilution) 240 pg/ml to 850 pg/ml for Yorkshire Pig EDTA Plasma (1/20 minimum dilution) |
| Minimum Quantifiable Concentration | Endogenous values as low as 120 pg/ml will be reported for information only with a % CV of approximately 60% in this range. |
| Maximum Quantifiable Concentration | 80 pg/ml to 1280 pg/ml for rat EDTA plasma |
| INTRA-ASSAY PRECISION in Human EDTA Plasma | Low 14% High 8% |
| INTER-ASSAY PRECISION in Human EDTA Plasma | Low 11% High 8% |
| ACCURACY | 6 normal human EDTA plasma samples were spiked with high, mid and low concentrations of rhVEGF. Mean % recoveries were: Low Mid High 106% 113% 99% 4 normal human serum samples were spiked with a high concentration of rhVEGF Mean % recovery: High 113% 3 rat EDTA plasma samples were spiked with high, mid and low concentrations of rhVEGF. Mean % recoveries in the quantitative range were: Low Mid High 82% 91% 99% 4 female and 4 male Yorkshire pig EDTA Plasmas were spiked with high, mid and low concentrations of rhVEGF. rhVEGF quantitation below 12 pg/ml (endogenous VEGF measured) will be reported for information only (mean % recovery below 12 pg/ml is approximately 60%). Mean % recoveries in the quantitative range were: Low Mid High n/a 86% 107% |
| SPECIFICITY | rhVEGF, IGF, TNE NGF, hGH, IFN, llblIla, rhuMAb VEGF, anti-VEGF MAb 3.5F8 were spiked into human EDTA plasma. Only the rhVEGF spike had measurable values above the endogenous VEGF serum levels. |

| | -continued |
|---|---|
| LINEARITY AND INTERFERENCE | rhVEGF was spiked into 6 different normal human EDTA plasma samples. Samples were serially diluted ½ to cover the range of the standard curve. 4 dilutions were made from each sample. rhVEGF values obtained were plotted against 1/dilution and the correlation coefficient ($R^2$) of a linear regression analysis was calculated. Samples were linear across the range of the standard curve.<br>n   Mean $R^2$   SD<br><br>6   0.996   0.005<br>rhVEGF was spiked in 3 rat EDTA plasma samples at high, mid and low concentration. Samples were linear across the high and mid quantitative range.<br>n   Mean $R^2$   SD   Spike<br><br>3   0.998   0.002   High<br>3   0.998   0.003   Mid<br>3   0.967   0.034   Low<br>rhVEGF was spiked into 8 EDTA pig plasma samples and serially diluted ½ to cover the range of the standard curve. 4 dilutions were made from each sample. Samples were linear across the range of the standard curve.<br>n   Mean $R^2$   SD<br><br>8   1   0.001 |
| SAMPLE STABILITY | 5 normal EDTA plasma samples were tested for freeze-and-thaw stability. Human EDTA plasma is stable for 3 freeze-and-thaw cycles. Mean % recoveries:<br>1X 101%<br>2X 101%<br>3X 93% |
| RUGGEDNESS/ ROBUSTNESS | pH profile indicates that the multi-site assay can tolerate pH's ranging from 6–9. No quantitation of rhVEGF at pH 4 and 5.<br>No effect on sample quantitation between a 1.5 and 16 hour sample incubation. (% difference in control recover: H ctrl 19%, L ctrl 16%). Assay performed at room temperature.<br>No effect on temperature incubation (1 hour vs. overnight at 37° C.) in VEGF quantitation of human plasma and serum samples. Mean % recoveries:<br>          1 hour   overnight<br><br>serum   113%   121%<br>plasma   115%   113% |
| ASSAY ACCEPTABILITY | |
| Matrix Controls | Westgard Multi-rules. ±2 SD from mean n (30% CV for Low Control) |
| Buffer Controls | n/a |
| Standard Curve: Correlation Coefficient | >0.994 |
| Precision (% CV) | <10% |
| Accuracy (% differences) | <20% |
| Regression Parameters | <20% CV |
| Samples | <20% difference between dilutions. |
| SPECIAL COMMENTS | Samples containing rhuMAb VEGF will interfere in the accurate quantitation of VEGF.<br>Various samples were tested to improve sample linearity of endogenous VEGF (intending to release VEGF from possible binding proteins). Increasing amount of NaCl from 0.5–1.5 M in combination with varying pHs as well as the addition of glycine or KSCN (pretreatment) or heat inactivation did not improve dilution linearity or increase VEGF measured. |

4. Discussion

Little is known about the levels or the circulating forms of VEGF in normal individuals during growth, pregnancy, and old age or in pathophysiological disease states. Herein is described the development and characterization of a sensitive, high-throughput assay capable of measuring various isoforms of VEGF and their levels in human plasma. This assay represents an important tool for measuring VEGF levels in both normal individuals and in various disease states.

The multi-site VEGF ELISA herein can measure 165/165, 165/110, 121/121, and 110/110 VEGF variants equally well With. this assay, higher plasma VEGF was detected in normal donors (192±68 pg/ml, n=50). For the same 18 cardiovascular patients, a significantly higher plasma VEGF above normal donors was detected (279±157 pg/ml, n=18, p<0.001). See FIG. 13 Indeed, monoclonal antibody MAb 3.5F8 plus affinity-purified polygonal antibody against an irrelevant protein did not generate any additional signal above that of MAb 3.5F8 alone. It is concluded that besides intact VEGF, other VEGF variants and isoforms are present in the circulation of both normal donors and cardiovascular patients. Ability to demonstrate that the receptor binding domain of VEGF is accessible for binding may be an important feature for any assay intended to understand the biological activity of VEGF in the circulation.

The fluorometric substrate, strep-β-gal/MUG, is preferred for use in the detection system so that the ELISA can detect endogenous VEGF levels in normal individuals. The use of this substrate and the determination of the best ELISA diluent resulted in much lower background absorbance, which was preferred to achieve the increase in the assay sensitivity.

The multi-site ELISA described herein is highly specific due to the choice of antibodies used for capture and detection. One of the coat antibodies, MAb 3.5F8, binds near the heparin binding region of VEGF (residues 111–165) and the other coat antibody, the rabbit polyclonal antibody binds VEGF. The detection antibody, MAb A4.6.1, binds in the KDR receptor binding region (residues 1–110) of the molecule, yielding a specific ELISA for VEGF.

The specificity of this multi-site ELISA will be important as the biology of VEGF is better understood. Keyt et al., supra (p. 7788) have demonstrated that the different VEGF variants examined in this study have varying bioactivities in vitro. Knowledge of assay specificity will also be extremely important in evaluating clinical data and comparing data between laboratories.

Published reports (Kondo et al., supra (1994), Takano et al., supra (1996); Rodriguez et al, supra) have noted that serum VEGF levels were elevated in cancer patients. Considering that angiogenesis is a general phenomenon in solid tumor progression, and that expression of VEGF, a tumor angiogenesis factor, is observed in a wide variety of tumor cells of various origins, measurement of circulating VEGF levels has potential as a non-invasive diagnostic marker for a wide spectrum of solid tumors.

In conclusion, a sensitive ELISA that measures most molecular forms of VEGF has been developed. In accordance with the present invention, antibodies are raised in animals against human VEGF, with the C-terminal specific antibody being a monoclonal antibody and the whole-VEGF-specific antibody being a polyclonal antibody, preferably affinity purified These two antibodies are used as coat antibodies (immobilized capture reagents) on a solid support such as microtiter plates The antibody used for detection can be either polyclonal antibodies or monoclonal antibodies provided they are specific for the KDR and FLT1 binding domain regions of human VEGF.

Accurate and sensitive ELISAs like the one described herein are deemed important in helping to understand VEGF levels in various disease states A better understanding of both VEGF levels and the dominant isoforms present in both normal individuals and in pathophysiological disease states will enhance knowledge of the role of VEGF in normal and pathologic angiogenesis.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A method for detecting multiple isoforms of vascular endothelial growth factor (VEGF) in a biological sample, comprising:
   (a) incubating a biological sample with a capture reagent immobilized on a solid support to bind multiple isoforms of VEGF to the capture reagent, wherein the capture reagent comprises a mixture comprising a polyclonal antibody that binds VEGF and a monoclonal antibody that specifically binds to amino acid residues 111–165 of human VEGF; and
   (b) detecting VEGF bound to the immobilized capture reagent by contacting the bound VEGF with a detectable antibody that binds to N-terminal amino acid residues 1–110 of VEGF.

2. The method of claim 1, wherein the biological sample is isolated from a human.

3. The method of claim 2, wherein the human is a vascular, diabetic, or cancer patient.

4. The method of claim 3, further comprising:
   (c) measuring an amount of VEGF detected in (b), wherein the amount is quantitated using a standard curve.

5. The method of claim 1, wherein the biological sample is plasma, serum, or urine.

6. The method of claim 1, wherein the capture reagent is immobilized in a weight ratio of about 0.8:1 to about 1.2:1 of monoclonal to polyclonal antibody.

7. The method of claim 6, wherein the weight ratio is about 1:1 of monoclonal to polyclonal antibody.

8. The method of claim 7, wherein the amount of monoclonal antibody immobilized is about 0.4 µg/ml and the amount of polyclonal antibody immobilized is about 0.4 µg/ml.

9. The method of claim 1, wherein the solid support is a microtiter plate.

10. The method of claim 1, wherein the detectable antibody is fluorescently labeled.

11. The method of claim 1, wherein the capture reagent monoclonal antibody is a murine monoclonal antibody.

12. The method of claim 11, wherein the capture reagent monoclonal antibody is MAb 3.5F8 produced by a hybridoma having ATCC Accession No. HB PTA-3499, or progeny thereof.

13. The method of claim 1, wherein the capture reagent polyclonal antibody is a rabbit or goat polyclonal antibody.

14. The method of claim 1, wherein the capture reagent polyclonal antibody is affinity purified.

15. The method of claim 1, wherein the detectable antibody is a monoclonal antibody.

16. The method of claim 15, wherein the detectable monoclonal antibody is a murine monoclonal antibody.

17. The method of claim 16, wherein the detectable monoclonal antibody is MAb A4.6.1 produced by a hybridoma having ATCC Accession No. HB 10709, or progeny thereof.

18. An immunoassay kit for detecting multiple isoforms of vascular endothelial growth factor (VEGF) in a biological sample, the kit comprising:
   (a) as a capture reagent, a mixture comprising a polyclonal antibody that binds VEGF and a monoclonal antibody that specifically binds to amino acid residues 111–165 of human VEGF; and
   (b) as a detection reagent, a detectable antibody that binds to N-terminal amino acid residues 1–110 of VEGF.

19. The kit of claim 18, further comprising purified VEGF as an antigen standard.

20. The kit of claim 18, wherein the capture reagent is immobilized on a solid support in a weight ratio of about 0.8:1 to about 1.2:1 of monoclonal to polyclonal antibody.

21. The kit of claim 20, wherein the weight ratio is about 1:1 of monoclonal to polyclonal antibody.

22. The kit of claim 21, wherein the amount of monoclonal antibody immobilized is about 0.4 µg/ml and the amount of polyclonal antibody immobilized is about 0.4 µg/ml.

23. The kit of claim 20, wherein the solid support is a microtiter plate.

24. The kit of claim 18, wherein the detectable antibody is fluorescently labeled.

25. The kit of claim 18, wherein the capture reagent monoclonal antibody is a murine monoclonal antibody.

26. The kit of claim 25, wherein the capture reagent monoclonal antibody is MAb 3.5F8, produced by a hybridoma having ATCC Accession No. HB PTA-3499, or progeny thereof.

27. The kit of claim 18, wherein the capture reagent polyclonal antibody is a rabbit or goat polyclonal antibody.

28. The kit of claim 18, wherein the capture reagent polyclonal antibody is affinity purified.

29. The kit of claim 18, wherein the detectable antibody is a monoclonal antibody.

30. The kit of claim 29, wherein the detectable monoclonal antibody is a murine monoclonal antibody.

31. The kit of claim 30, wherein the detectable monoclonal antibody is MAb A4.6.1, produced by a hybridoma having ATCC Accession No. HB 10709, or progeny thereof.

* * * * *